(12) United States Patent
Klimaszewska et al.

(10) Patent No.: US 6,200,809 B1
(45) Date of Patent: Mar. 13, 2001

(54) MATURATION OF SOMATIC EMBRYOS

(75) Inventors: Krystyna Klimaszewska; Benjamin C. Sutton, both of Vancouver; Daniel R. Polonenko, Coquitlam; David R. Cyr, Vancouver; Thomas F. Stodola, Burnaby, all of (CA)

(73) Assignee: Cellfor Inc., Vancouver (CA)

( * ) Notice: Subject to any disclaimer, the term of this patent is extended or adjusted under 35 U.S.C. 154(b) by 0 days.

(21) Appl. No.: 09/135,264

(22) Filed: Aug. 17, 1998

Related U.S. Application Data
(60) Provisional application No. 60/078,285, filed on Mar. 17, 1998.

(51) Int. Cl.⁷ .............................. C12N 5/00; C12N 5/04; A01H 4/00; A01H 7/00
(52) U.S. Cl. ................... 435/422; 435/410; 435/420; 435/430.1; 435/431; 800/319
(58) Field of Search .................... 435/422, 410, 435/420, 430, 430.1, 431; 800/319

(56) References Cited

U.S. PATENT DOCUMENTS

| | | | |
|---|---|---|---|
| 3,920,436 | * 11/1975 | Janssen | 71/65 |
| 4,217,730 | * 8/1980 | Abo El-Nil | 47/58 |
| 4,615,141 | * 10/1986 | Janick et al. | 47/576 |
| 4,777,762 | * 10/1988 | Redenbaugh et al. | 47/57.6 |
| 4,957,866 | * 9/1990 | Gupta et al. | 435/240.4 |
| 5,034,326 | * 7/1991 | Pullman et al. | 435/240.4 |
| 5,036,007 | * 7/1991 | Gupta et al. | 435/240.45 |
| 5,041,382 | * 8/1991 | Gupta et al. | 435/240.45 |
| 5,183,757 | 2/1993 | Roberts | 435/240.49 |
| 5,238,835 | 8/1993 | McKersie et al. | 435/240.45 |
| 5,294,549 | * 3/1994 | Pullman | 435/240.45 |
| 5,413,930 | * 5/1995 | Becwar et al. | 435/240.49 |
| 5,464,769 | * 11/1995 | Attree et al. | 435/240.1 |
| 5,523,230 | * 6/1996 | Smith | 435/240.45 |
| 5,563,061 | 10/1996 | Gupta | 435/240.45 |
| 5,565,355 | * 10/1996 | Smith | 435/240.49 |

FOREIGN PATENT DOCUMENTS

| | | | |
|---|---|---|---|
| 60707/94 | 10/1994 | (AU) | C12N/5/00 |
| B3714893 | * 11/1994 | (AU) . | |
| 60707 | * 10/1999 | (AU) | C12N/5/00 |
| 2064697 | * 4/1996 | (CA) . | |
| 0300730 | * 2/1989 | (EP) . | |
| WO8704044 | * 7/1987 | (WO) . | |
| WO8905575 | * 6/1989 | (WO) . | |
| WO 91/01629 | 2/1991 | (WO) . | |
| WO9311660 | * 6/1993 | (WO) . | |
| WO9637095 | * 11/1996 | (WO) . | |

OTHER PUBLICATIONS

Durzan et al, Plant Science. 52:229–235, 1987.*
Sokal and Rohif, Biostatistics, Freeman and Company, p. 333, 1987.*
Krystyna Klimaszewska and Dale R. Smith, "Maturation of somatic embryos of *Pinus strobus* is promoted by high concentration of gellan gum," *Physiologia Plantarum* 100:949–957, 1997.
Dane R. Roberts et al., "Abscisic acid and indole–3–butyric acid regulation of maturation and accumulation of storage proteins in somatic embryos of interior spruce," *Physiologia Plantarum* 78: 355–360, Copenhagen 1990.
John D. Litvay et al., "Influence of a loblolly pine (*Pinus taeda* L.). Culture medium and its components on growth and somatic embryogenesis of the wild carrot (*Daucus carota* L.)," *Plant Cell Reports* (1985)4:325–328.
S.M. Attree et al., "Enhanced Maturation and Desiccation Tolerance of White Spruce [*Picea glauca* (Moench) Voss] Somatic Embryos: Effects of Non–plasmolysing Water Stress and Abscisic Acid," *Annals of Botany* 68, 519–525, 1991.
M.R. Becwar et al., "Initiation of embryogenic cultures and somatic embryo development in loblolly pine (*Pinus taeda*)," *Can. J. For. Res.* vol. 20, 1990, pp. 810–817.
Danielle Julie Carrier et al., "(+)–ABA Content and Lipid Deposition in Interior Spruce Somatic Embryos," *In Vitro Cell. Dev. Biol.–Plant* 33:236–239, Jul.–Aug.–Sep. 1997.
Jens I. Find, "Changes in endogenous ABA levels in developing somatic embryos of Norway spruce (*Picea abies* (L.) Karst.) in relation to maturation medium, desiccation and germination," *Plant Science* 128 (1997), 75–83.
K. Klimaszewska et al., "*Larix laricina* (tamarack): somatic embryogenesis and genetic transformation," *Can. J. For. Res.* vol. 27, 1997, pp.538–550.
Plant Science; vol. 63; Krystyna Klimaszewska; "Plantlet Development from Immature Zygotic Embryos of Hybrid Larch Through Somatic Embryogenesis"; 1989; pp. 95–103.
Can.J.For.Res.; vol. 20; 1990; von Aderkas et al.; "Diploid and Haploid Embryogenesis in *Larix Leptolepis, L. Decidua,* and Their Reciprocal Hybrids"; pp. 9–14.

(List continued on next page.)

*Primary Examiner*—Bruce H. Campbell
*Assistant Examiner*—Anne Marie Grünberg
(74) *Attorney, Agent, or Firm*—Robert H. Barrigar; Barrigar Intellectual Property Group

(57) ABSTRACT

A method of developing and maturing somatic embryos in a growth environment, which method comprises manipulating the water availability of the growth environment using a physical means of control. The invention also provides a growth environment for maturing somatic embryos, wherein the water potential of the embryogenic tissue is manipulated to optimize somatic embryo development and maturation. The invention further relates to a somatic embryo matured by the method of the invention. In the invention, a physical means of control is used to affect the water potential of the embryogenic tissue and developing somatic embryos growth medium, rather than a chemical means such as the introduction of PEG, to stimulate the maturation of the embryos. The physical means may be operated, for example, by separating the somatic embryos from the growth medium by a porous support, or by introducing a gelling agent (e.g. gellan gum) into the growth medium in larger than normal quantities.

24 Claims, 2 Drawing Sheets

OTHER PUBLICATIONS

Can.J.For.Res.; vol. 27; 1997; Klimaszewska et al.; "*Larix Laricina* (Tamarack): Somatic Embryogenesis and Genetic Transformation"; pp. 538–550.

Santakumari, et al. "Reversal of triazole–induced stomatal closure by gibberellic acid and cytokinins in *Commelina benghalensis,* (1987)," Physiol. Plant 71:95–99.

T. Senaratna et al. "Artificial Seeds of Alfalfa (*Medicago Sativa* L.). Induction of Desiccation Tolerance in Somatic Embryos," In Vitro Cell Cell Dev. Biol, 26, 85–90, (1990).

K. Anandarajah, B.D. McKersie, S.R. Bowley and T. Senaranta, Development of Hybrid Alfalfa, University of Guelph Department of Crop Science Annual Report, (1989), (Ontario Agricultural College, Guelph, Ontario).

Norman et al., (1983), Inhibition of Abscisic Acid Biosynthesis in *Cercospora rosicola* by Inhibitors of Gibberellin Biosynthesis and Plant Growth Retardants, Plant Physiol. 71:15–18.

Obendorf, et al., (1986), Somatic Embryogenesis from Cotyledonary Tissues of Soybean and Maturation to a Desiccation Tolerant State, In Vitro, vol. 22(3):53A.

Barwale, et al., Plant regeneration from callus cultures of several soybean genotypes via embryogenesis and organogenesis, (1986) Planta 167:473–481.

Gray, et al., (1987), Desiccated Quiescent Somatic Embryos of Orchardgrass for Use as Synthetic Seeds, In Vitro Cellular & Developmental Biology (23), 29–33.

"A Surprise in the Test Tube," Research 5, No. 24 (1989–90) (ISSN 0841–9493).

J. Buchheim et al., "Maturation of Soybean Somatic Embryos and the Transition to Plantlet Growth," Plant Physiol. 89, 768–775 (1989).

W. Cheliak et al., Can. J. Forest Res. 20, 454 (1990).

Stress Responses in Plants: Adaptation and Acclimation Mechanisms, pp. 113–146, Morgan, "6. Effects of abiotic Stresses on Plant Hormone Systems," 1990 Wiley Liss, Inc.

HortScience, vol. 22(5), Oct. 1987, pp. 803–809, Redenbaugh, et al., "Encapsulation of Somatic Embryos in Synthetic Seed Coats."

Advanced Plant Physiology, 1984, edited by Malcolm B. Wilkins, p. 85.

Van Acker, S., "A comparison of desiccation tolerance in zygotic and somatic embryos of alfalfa (*Medicago sativa* L.)," Masters Thesis, University of Guelph, Jul., 1992, (See especially p. 56).

Marsolais, A. A., et al., "Somatic embryogenesis and artificial seed production in Zonal (*Pelargonium x hortorum*) and Regal (*Pelargonium x domesticum*) geranium," Can. J. Bot., vol. 69, pp. 1188–1193 (1991).

De, R. and Kar, R.K., Effect of Water Stress on Protein, Amino Acids and Protein Contents in Germinating Mingbean Seeds, Indian J. Plant Physiol. vol. XXXVII, p. 116–118 (1994).

K.R. Redenbaugh, "Application of Artificial Seed to Tropical Crops" Paper presented at the 84th ASHS Annual Meeting of 34th ISTH Annual Congress, Nov. 12, 1987, Orlando, Florida.

C.E. Flick et al., "Handbook of Plant Cell Culture, vol. 1,", Ch. 2, "Organogenesis" p. 13, 62, 63 (1983), Macmillan Publishing Co.

P.V. Ammirato, "Handbook of Plant Cell Culture, vol. 1", Ch. 3, "Embryogenesis", p. 82, 106, 108 (1983), Macmillan Publishing Co.

Attree, S. N., Fowke, L.C. (1991) Micropropagation through somatic embryogenesis in conifers. In, Biotechnology in agriculture and forestry, "High–tech and Micropropagation", vol. 17, pp. 53–70, Bajaj, Y.P.S. ed. Springer–Verlag, Berlin.

Cornu et al., Aspects de l'embryogenése somatique chez le mélèze, France Soc. Bot. 137:25 (1990).

Fourre et al., In Vitro Germination of Encapsulated *Picea abies* (L.) Karst. Somatic Embryos: Preliminary Results, Med. Fac. Landbouww. Rijksuniv. Gent. 56(4a): 1449 (1991).

Roberts, D.R., Sutton, B.C.S. and Flinn, B.S., 1990b. Synchronous and high–frequency germination of interior spruce somatic embryos following partial drying at high relative humidity. Canadian Journal of Botany 68, 1086–1090.

Chowdhury et al., The Embryogeny of Conifers: A Review, Phytomorphology 12:313 (1962).

Tautorus et al., Somatic embryogenesis in conifers, Canadian Journal of Botany, 69: 1873 (1991).

Feirer et al., Aspects de l'embryogenésé chez le méléze, Plant Cell Reports 8: 207(1989).

Joy et al., "Development of White Spruce Somatic Embryos. I Storage Product Deposition", In Vitro Cell Dev. Biol. 27: 32 (1991).

Attree, S.M., et al., "Production of Vigorous Dessication Tolerant White Spruce (*Picea Glauca* [*Moench.*] Voss.) Synthetic Seeds in a Bioreaction", Plant Cell Reports (1994), 13:601–606.

Hakman et al., 1988, Somatic embryogenesis and plant regeneration from suspension cultures of *Picea glauca* (White Spruce), Physiol. Plant. 72(3): 579–587.

Becwar et al., 1987, Somatic embryo development and plant regeneration from embryogenic Norway spruce callus, TAPPI J 70(4): 155–160.

Hammatt et al., 1987, Somatic Embryogenesis and Plant Regeneration from Cultured Zygotic Embryos of Soybean (*Glycine max* L. Merr.), J. Plant Physiol. 128(3): 219–226.

Boulay et al., 1988, Development of somatic embryos from cell suspension cultures of Norway spruce (*Picea abies* Karst.), Plant Cell Reports, 7:134–137.

Bewley, J.D. and Black, M. (1985) "Maturation Drying, The Effects of Water Loss on Development in Seeds"; Physiology of Plant Development, Chapter 2.4; Plenum Press N.Y.; pp. 70–73.

Becwar, M. R. et al., "Maturation, Germination, and Conversion of Norway Spruce Somatic Embryos to Plants" (1989), In Vitro Cell & Dev. Biol. 25: 575–580.

W.A. Parrott et al., Optimization Of Somatic Embryogenesis And Embryo Germination In Soybean, In Vitro Cellular & Developmental Biology, vol. 24, No. 8, (1988).

D.J. Durzan et al., Somatic Embryogenesis And Polyembryogenesis In Douglas–Fir Cell Suspension Cultures, Plant Science, 52 (1987) 229–235.

J.G. Carman, Improved somatic embryogenesis in wheat by partial simulation of the in–ovulo oxygen, growth–regulator and desiccation environments, Planta (1988) 175:417–424.

I. Hakman et al., Plantlet Regeneration through Somatic Embryogenesis in *Picea abies* (Norway Spruce), Institute of Physiological Botany, University of Uppsala, J. Plant Physiol. vol. 121, pp. 149–158 (1985).

J.A. Buchheim et al., Maturation of Soybean Somatic Embryos and the Transition to Plantlet Growth, Plant Physiol., (1989) 89, 768–775.

A.R. Kermode et al., The Role of Maturation Drying in the Transition from Seed Development to Germination I Acquisition of Desiccation–Tolerance and Germinability During Development of *Ricinus Communis* L. Seeds, J. Experimental Botany, vol. 36, No. 173, p. 1906–1915, (1985).*

A.R. Kermode et al., Developing Seeds of *Ricinus Communis* L., When Detached and Maintained in an Atmosphere of High Relative Humidity, Switch to a Germinative Mode without the Requirement for Complete Desiccation, Plant Physiol, (1989) 90, 702–707.*

Schuller et al. (1989), Somatic embryogenesis from seed explants of *Abies alba,* Plant Cell, Tissue & Organ Culture, vol. 17, pp. 53–58.*

Becwar et al., (1988), Development and Characterization of In Vitro Embryogenic Systems in Conifers, Somatic Cell Genetics of Woody Plants, Editor M.R. Ahuja, Kluwer Acadenic Press, pp. 1–18.*

Lelu, (1988), Annales de Researches Silvicoles, AFO–CEL, Paris, pp. 35–47, with English translation.*

Lelu et al., (1987), C.R. Acad. Sci., Paris, 305, Series 3, pp. 105–109.*

Finer et al., (1989), Initiation of embryogenic callus and suspension cultures of eastern white pine (*Pinus strobus* L.), Plant Cell Reports, vol. 8: pp. 203–206.*

Verhagen et al., Norway spruce somatic embryogenesis: high–frequency initiation from light–cultured mature embryos, Plant Cell, Tissue & Organ Culture, vol. 16, pp. 103–111.

Gupta et al. (1987), Somatic Embryos from Protoplasts of Loblolly Pine Proembryonal Cells, Bio/Technology, vol. 5, pp. 710–712.

Flinn et al., Evaluation of Somatic embryos on interior spruce. Characterization and developmental regulation of storage proteins, Physiologia Plantarum 82:624–632, Copenhagen (1991).

Seedman's Digest, "Artificial Seed Targets High–Value Crops," (Apr., 1987), vol. 38(4), pp. 6–7.

Senaratna, T. et al., "Desiccation Tolerance of Alfalfa (*Medicago Sativa* L.) Somatic Embryos Influence of Abscisic Acid, Stress Pretreatments and Drying Rates", Plant Science, 65 (1989), pp. 253–259.

* cited by examiner

MATURATION OF SOMATIC EMBRYOS

CROSS-REFERENCE TO RELATED APPLICATIONS

This application is related to our prior provisional patent application Ser. No. 60/078,285 filed Mar. 17, 1998.

BACKGROUND OF THE INVENTION

The present invention relates to the field of somatic embryogenesis and, in particular, to methods of manipulating the maturation of somatic embryos within culture vessels.

Recently, somatic embryogenesis has gained attention as it offers a possible low-cost means for clonal reproduction of large numbers of plants of various species. The steps of somatic embryogenesis, including the initiation and proliferation of embryogenic cultures from explant tissues, have been documented in the art for many plants, including angiosperms and gymnosperms. Simply, the method of somatic embryogenesis involves the selection of an explant of a desired plant. The explant is removed from the parent plant tissue by excision and then subsequently cultured on at least one medium to produce a cell mass capable of further differentiation or development. The cell mass can be maintained and proliferated in the undifferentiated state indefinitely, or manipulated to stimulate differentiation into immature somatic embryo structures which can then be further cultured to form mature somatic embryos. Mature somatic embryos can be harvested and germinated immediately, or dried and then germinated, or dried and stored until required for germination.

Somatic embryos are known to be stimulated to develop and mature in culture if environmental stresses are imposed, such as heat, nutrient depletion, solute-based water stress or increased levels of the plant hormone abscisic acid ("ABA"), whether added exogenously or induced endogenously (see U.S. Pat. No. 5,238,835 to McKersie et al., the contents of which are incorporated herein by reference, said patent referred to hereinafter as the McKersie patent). The McKersie patent discloses the use of stress, including osmotic, nutrient, water and heat stresses among others, to trigger the endogenous production of ABA within somatic embryogenic cultures.

Due to the fact that somatic embryos develop without the surrounding nutritive tissues, i.e. megagametophytes in gymnosperm species and endosperm in angiosperm species, and protective seed coats normally present in zygotic seeds, research has focused on comparing the types and quantities of storage reserves (e.g. lipids, proteins, amino acids, monosaccharides and polysaccharides) produced in somatic embryos with those (average levels) in zygotic seeds of the same species, and on assessing their potential for improving the ease of handling, storage stability, and germination vigour of somatic embryos. Exogenous applications of ABA, and solutes such as polyethylene glycol ("PEG"—most commonly having a molecular weight of 4,000, but possibly ranging in molecular weight from 2,000 to 8,000) have been proposed as useful adjuncts for enhancing the levels of storage reserves in plant cells and in particular, somatic embryos. Specifically, it has been shown that ABA or PEG can be used to promote or otherwise enhance the maturation step of the somatic embryogenesis process with gymnosperms, e.g. conifers, and to reduce the occurrence of precocious germination during the maturation step (Roberts et al. 1990; Attree et al. 1991; Flinn et al. 1991; Carrier et al. 1997). The embryos which result from PEG and/or ABA facilitated maturation may be larger than their zygotic counterparts and may exhibit greater storage protein and lipid reserves (Flinn et al., 1991; 1995 U.S. Pat. No. 5,464,769 to Attree & Fowke, the contents of which are incorporated herein by reference, and said patent referred to herein as the Attree patent). Conifer somatic embryos produced on media containing PEG and having enhanced lipid levels and reduced moisture contents have been disclosed (the Attree patent). The use of ABA-amended media for the production of conifer somatic embryos with these same attributes have also been previously disclosed (Flinn et al. 1991: Carrier et al. 1997).

Accordingly, it is well known to increase the solute concentration in embryogenic culture media by the incorporation of permeating osmotica (i.e. sugars such as sucrose, mannitol or salts). However, there are problems inherent in these agents being absorbed by the symplast of the plant cells which leads to the development of atypical and poorly germinating embryo products. The alternative is to incorporate into the culture media, non-permeating high-molecular-weight compounds such as PEG or dextran (the Attree Patent). However, it has been recently disclosed that non-permeating high-molecular-weight solutes such as PEG and dextran do not reliably produce viable and useful embryos for all conifer species (Find et. al., 1997; Klimaszewska & Smith, 1997). It has also been disclosed that, contrary to common belief, small amounts of high molecular weight PEG (8000) enters the cell protoplast or alternatively, bind to the plasmalemma of *Pinus taeda* and sorghum callus cells when cultured on medium containing PEG (Newton et al., 1990). As well, concerns were raised about the adverse action of some unknown organic impurities in commercial PEG sources in the cellular metabolic processes (Plant and Federman, 1985).

A large group of patents held by the Weyerhaeuser Corporation discloses altering the osmotic potential of the medium during maturation of conifer somatic embryos using solutes. One representative patent is U.S. Pat. No. 5,563,061 which describes a multi-phase culturing process in which differently "tailored" media are used at each phase of somatic embryogenesis. During the second and third phases, the early stage embryos are grown for a defined time period on a culture medium containing a higher osmolality than that used in the induction phase. The osmotic potentials in the phase-two and phase-three media are altered by the incorporation of solutes such as sugars, PEG, sorbitol, myo-inositol, mannitol, and lactose.

Although the use of PEG or other similar non-permeating solutes discussed above as well as others known in the art, have been used successfully to mimic the chemical, hormonal, and environmental triggers of maturation in producing mature somatic embryos for some plant species including conifers, a large proportion of the embryos produced are atypical and not useful for germination and further propagation. Therefore, it is desirable to avoid the use of PEG and other similar non-permeating solutes for somatic embryogenesis with conifers generally, and with spruce and pine species in particular.

BRIEF SUMMARY OF THE INVENTION

It is an object of the present invention to obviate or mitigate the above disadvantages.

Another object of the invention is to produce high numbers of high-quality plant somatic embryos capable of germination and subsequent conversion to complete and fully functional plants.

A further object of the invention is to minimize the production of unacceptable atypical plant somatic embryos.

The present invention provides a method of developing and maturing somatic embryos in a growth environment having a water potential, which method comprises exposing an embryogenic culture of embryogenic tissue or developing and maturing embryos to an aqueous liquid maturation medium, and allowing said embryogenic culture to develop into mature somatic embryos, wherein a physical means is used to affect the availability of water in the growth environment for uptake by said embryogenic culture in a manner such that resulting water potentials of the developing and maturing somatic embryos are reduced below the water potential of the growth environment.

The invention also provides a method of manipulating the availability of water for uptake during the development and maturation of somatic embryos in a culture vessel, which comprises placing an aqueous liquid maturation medium in the vessel, positioning a porous support carrying a culture of the embryos on the liquid medium such that there is no direct contact between the medium and the culture, sealing the vessel with a cover, and allowing said embryos to develop and mature.

The present invention also provides a growth environment suitable for maturing somatic embryos, wherein the water potential of the embryogenic tissue is manipulated to initiate and optimize embryo development and maturation.

Further, the present invention provides somatic embryos prepared according to the manipulation methods and using the growth environments described herein.

By the term "water potential of the embryogenic tissue and/or somatic embryos" the applicants mean the total water potential which is a sum of osmotic potential, turgor potential, and matric potential of the cells of embryogenic tissue and/or somatic embryos.

By the term "matric potential" the applicants mean the effect of water molecules physically binding or adhering to surfaces, on the availability of water for uptake by embryogenic cultures and/or somatic embryos. In connection with a physical support for an embryogenic culture, it will be noted that, the coarser or more porous the material, the less water will be physically bound to the fibers, etc. A more dense or "fine" (i.e. less porous) material will physically bind more water. When comparing equally tall blocks of two materials of different degrees of coarseness, there will be less capillarity in the coarse block than in the fine block. Consequently, water will be drawn up closer to the top of the fine block, and therefore, be more available to a culture supported on the fine block than the coarse block. The result is that the culture on the coarse block will be exposed to more negative water potential and therefore will be under greater water stress than the one on the fine block. The porosity of the material is sometimes referred to as the gradient of the matric water potential.

By the term "water availability", the applicants mean the availability of water for uptake by the maturing embryo, as opposed to water that may be unavailable due to association with a matrix or the like. Water availability can be affected by physical means of control, including (but not limited to) pressure, matric and gravitational effects. The effects of physical means on water availability are separate and distinct from the effects of solutes and their resulting osmotic potentials.

By the term "growth environment", the applicants are referring herein to one or both of the liquid maturation medium, and the physical support (cross-linked polymeric agents, porous materials, and the like) on which or in which the embryogenic culture is placed. The manipulation and control of the water potential of the embryogenic tissue and/or somatic embryos is achieved without significant changes to the solute concentrations within the maturation medium. In essence, the key to the method of the present invention is the ability to precisely apply, manipulate and control the water potential of the embryogenic tissue and/or somatic embryos during maturation using a physical means. Most commonly, although not necessarily, the water potential of the embryogenic tissue and/or somatic embryos is reduced by the physical means of controlling water availability from the liquid maturation medium. The applicants have chosen the term "physical means" in order to distinguish the manipulation techniques contemplated as being within the scope of the invention from the use of solute manipulation of the maturation medium disclosed in the references discussed above. Accordingly, embryo development using the methods of the present invention, is stimulated without the concomitant disadvantages (i.e., poor embryo quality, poor germination vigour) found when embryo maturation is affected by altering the concentration in the liquid culture medium, of each solute alone or in combination, said solutes including solutes such as PEG, dextran, sugars and the like, whether permeating or non-permeating. In the present invention, certain magnitudes of water potentials within embryogenic tissues and/or somatic embryos can be achieved through physical means that reduce the water potentials below that of the culture medium. This allows precise reductions in the water potentials without increasing the concentration of osmotically active solutes in the liquid medium which is accompanied by negative effects on somatic embryo development, maturation, and germination. It has been found that certain critical magnitudes of water potentials achieved through manipulation of solute concentrations in culture media, interfere with or otherwise impede embryo development and maturation (Klimaszewska et al., 1997).

The physical means of controlling the water potentials of embryogenic tissues and/or somatic embryos may be exerted, for example, by separating the culture from the growth medium by a porous support, or by introducing a gelling agent into the growth medium.

The present invention is applicable during the maturation of somatic embryos from a wide range of plant species, and enables the embryos to be maintained successfully in culture vessels for longer periods of time than has been shown in the methods currently known and practised. This extended maturation stimulates the development of superior, high quality embryos with lower water contents than heretofore has been achieved. In addition, the methods disclosed in the present invention for manipulating the water potentials within embryogenic tissues to affect the initiation and maturation of somatic embryos can be readily practised in conjunction with any somatic embryogenic culture media.

Furthermore, and equally importantly, the somatic embryos prepared using the maturation method described herein are amenable to further drying by desiccation techniques commonly known and practiced in the art, to water content levels that approximate those of natural zygotic seeds. The subsequent germination success rates of somatic embryos produced by the methods described herein also compare favourably to those for natural zygotic seeds.

DETAILED DESCRIPTION OF THE INVENTION

Figure 1A:
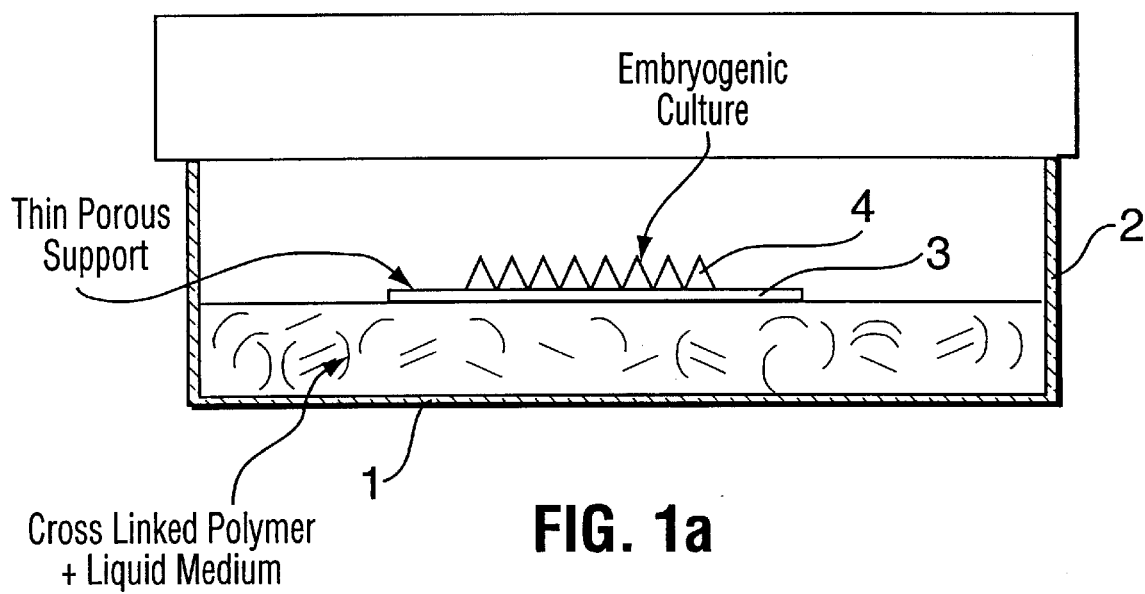
FIG. 1A and FIG. 1B are schematic drawings respectively showing a side view and a top plan view of one embodiment of a growth environment as contemplated within this invention, used to obtain the results in Examples 14. The growth environments in these examples consisted of substrates containing fixed volumes of liquid growth medium and varying concentrations of crosslinked-polymeric agents. The embryogenic cultures were separated from the substrate by a thin porous support.

The present invention provides methods by which a growth environment of a somatic embryogenic culture may be manipulated during the maturation phase in order to control, as precisely as required, the water potential and thereby the water availability to the embryo culture. As already noted, by "growth environment", the applicant is referring herein to one or both of the aqueous liquid maturation medium, and the physical support (cross-linked polymeric agents, porous materials, and the like), if any, on which or in which the embryogenic culture is placed.

It is contemplated within the scope of this invention that water potential of the embryogenic tissue be manipulated during maturation of somatic embryos by one of a number of suitable means as described further herein below. The key to the invention is that this manipulation or control of the tissue water potential is achieved without manipulating the solute concentrations in the medium. Preferably, the solute concentrations are optimized within normal ranges for development of the embryos, and then the water availability to the cultures is manipulated by physical means to stimulate optimum maturation.

Although it is desirable to control (i.e. generally reduce) the amount of water available to a somatic embryogenic culture, the provision of some "free" water to the culture is necessary to enable the essential biological activity required for embryo maturation to occur. "Free" water refers specifically to water molecules that can be directly absorbed by plant cells and incorporated into metabolic pathways and physiological processes. The availability of "free" water, however, does not depend only on the water content of a culture medium; it is a complex function of physico-chemical adsorptive and solution factors. Water adsorbed onto surfaces may or may not be available for absorption by plant cells, depending on how tightly the individual water molecules are adsorbed onto the physical surface of a structure, and on how effective the plant cells are in removing water molecules attached to surfaces. By "surfaces", the applicant is referring to both the surface walls of containers into which culture media is placed, as well as the surfaces of any physical supports onto which or within which the embryogenic cultures are placed for the purpose of developing and/or maturing embryos. The points of attachment of water molecules to surfaces are called the meniscus. The effect of adsorption on water activity is often called the "matric effect", the matrix of substances or materials adsorbing the water at the meniscus, is directly responsible for reducing water availability for absorption and incorporation into biological processes by plant cell cultures.

Also, when solutes are dissolved in water, they become more or less hydrated i.e., chemically attached to individual water molecules. Water molecules that become attached to solutes are no longer "free" water molecules but rather, are "bound" or unavailable for incorporation into metabolic pathways. The degree to which solutes become hydrated, e.g., within a culture medium, will effect the availability of "free" water for uptake and incorporation by the embryogenic plant cultures. The effects of solute interactions with individual water molecules, on the availability of "free" water as referred to by the term "water activity," is then called the "osmotic effect."

The ways in which water availability are influenced by adsorption and solution factors may also be referred to as the "water potential." Another way to put it is that water potential is a measure of the specific chemical activity of water which indicates its freedom to interact with or be used by biological systems, and thereby determines water availability.

A somatic embryogenic culture, separated from direct contact with the culture medium, i.e. the source of water and nutrient (solute), by placement on a porous support as contemplated within one embodiment of the present invention, will only have a certain amount of "free" water available to it. The porous material will adsorb water and the avidity of this adsorption is determined by the physical and chemical, i.e., physico-chemical properties of the material. Accordingly, the amount of water available to the embryos supported on a porous medium is a function of one or more of the following:

1. The porosity of the support material i.e., the diameters, lengths and volumes of airspaces, through which liquids and air can flow within the physical structure of the support material.
2. The hydrophilic or hydrophobic properties of the materials comprising the physical support. Porous supports comprised of materials with hydrophilic properties tend to attract and adsorb water molecules resulting in concave-shaped meniscus, while porous supports comprised of materials with hydrophobic properties tend to repel water molecules and form convex meniscus.
3. The height of the support material i.e. the degree of separation of the embryogenic culture from the medium. This is shown by numeral 22 in FIG. 3 and is discussed further below.
4. The volume of liquid medium within the culture vessel (per FIGS. 2 & 3), which is directly related to height as described further below; or the volume of water held in a porous membrane (per FIG. 1) placed between the embryogenic culture and the physical support material.

The diameter and length of a pore structure comprised by hydrophilic materials will strongly attract and adsorb water molecules thereby creating a partial vacuum within the pore that will draw water upwards against the forces of gravity; this process is often referred to as cavitation. In contrast, pore structures comprised of hydrophobic materials will repel water and consequently, will not support the formation of partial vacuums within the pore resulting in minimal water movement upwards as a consequence of cavitation. The diameter and length of the individual pore structures combined with their three-dimensional arrangements and hydrophilic/hydrophobic properties significantly affect the degree of cavitation within the porous support which in turn, directly impacts on the ease and rate, as well as the height of capillary movement of solutions through the porous support.

The porous support may comprise many different types of materials, therefore, it is not intended that the present invention be limited to any one type of hydrophilic or hydrophobic material, or to certain arrays or combinations of physical materials to the exclusion of others. The most important features are that the physical support be "porous" in that it facilitates the movement of solutions through absorption and/or cavitation, that it provides a heterogenous matrix consisting of solid, liquid and air phases, for support of the embryogenic culture, and that it be non-toxic to the embryogenic culture. Some examples of suitable porous support structures include but are not restricted to:

1 different-sized, regular or irregular-shaped cell-like structures formed through natural or synthetic extrusions as exemplified by, but not restricted to foams or sponges, in which water flows from cell to cell by the processes of absorption and/or adsorption and/or saturation and/or cavitation,
2. regular or irregular interwoven networks of solid tube-like structures, e.g., fibres, of natural or synthetic origin as exemplified by, but not restricted to screens, filters, and absorbant tissues, in which water flows among the networks of solid fibres by the processes of absorption and/or adsorption and/or saturation and/or cavitation,
3. regular or irregular interwoven networks of hollow tube-like structures, e.g., fibres, of natural or synthetic origin as exemplified by, but not restricted to screens, filters, and absorbant tissues, in which water flows within and through the hollow fibres as well as among the networks of hollow fibres by the processes of absorption and/or adsorption and/or saturation and/or cavitation, and
4. regular or irregular interwoven networks of mixtures of hollow and solid tube-like structures, e.g., fibres, of natural or synthetic origin as exemplified by, but not restricted to screens, filters, and absorbent tissues, in which water flows within and through the hollow fibres as well as among the networks of hollow and solid fibres by the processes of absorption and/or adsorption and/or saturation and/or cavitation.

It is preferred that the maturation medium be in liquid form; however, in terms of composition, it may be selected from any basal media known and applied in somatic embryogenesis, including but not limited to modified Litvay medium (Litvay et al. 1985), MSG medium (Becwar et al. 1990) and DCR medium (Gupta and Durzan 1985). Generally, basal media containing sucrose and other osmotic and nutritive solutes are used for the processes inherent in somatic embryogenesis. For maturation of somatic embryos, most commonly, sucrose is used in the range of 0.1 M to 0.4M, and the media consequently typically have osmolalities in the range of approximately 150 to 480 mmol kg$^{-1}$ (for example, see Klimaszewska et al., 1997). The water potentials of the media in these examples are in the range of −0.37 MPa to −1.20 MPa.

Osmolalities of the media can be adjusted with addition of non-permeating osmotic agents such as PEG in order to reduce water potential to about −1.5 MPa. This commonly results in unpredictable and infrequent somatic embryo maturation, and subsequently, low rates of germination success (see, for example, the maturation of Larix spp. somatic embryos in Klimaszewska et al., 1997; also, see Tables 3, 12 and 13 in this application).

The exact level of water potential which is optimal for each plant species, varies with species. After somatic embryos have been developed and matured in various culture systems including gelled substrates or physical supports containing liquid media, further reductions in water potentials have been employed in the prior art to achieve further desiccation of somatic embryos. The procedures for reducing relative humidities of the air surrounding harvested somatic embryos are well-known (for example the McKersie patent; and 1993 U.S. Pat. No. 5,183,757 to Roberts, the contents of which are incorporated herein by reference, and said patent referred to herein as the Roberts patent). Typically, initial relative humidities of more than 85% are used to create water potentials in excess of −20 MPa. Subsequently, if desired, greater levels of somatic embryo desiccation may be achieved by using relative humidities of approximately 85% or less, which will provide water potentials of −20 MPa or less.

In one embodiment of the present invention, the water potential of the embryogenic tissue is manipulated not by separating the culture from the medium, but by increasing the concentration of a gelling agent in the medium above the level used in the induction and development media. It has been found that as the concentration of gelling agent in the maturation medium increases, the availability of water decreases, thereby imposing reduction in water potential within the embryogenic culture and/or somatic embryos. The magnitude of the water potential within the embryogenic cultures and/or somatic embryos can be precisely controlled by varying the concentration of the gelling agent used to prepare the medium.

A gelling agent, once mixed with a solvent, gives rise to a complex but homogenous physical matrix network in which the water plus the inorganic salts, sucrose, growth regulators, vitamins etc., are trapped. The preferred increase in gelling agent concentration depends, to some extent, on the type of agent used. For gellan gum, this generally means amounts of more than about 0.4%. For agars, this generally means amounts of more than about 0.6% (e.g. MBI-1 agar), 0.8% (Difco-Bacto agar), or 1.0% (MBI-2 agar).

More specifically, it has been found that the concentration of gellan gum (marketed under the names Gelrite® and Phytagel®) may be increased in the maturation medium to within the range of 6 g/l to 12 g/l, most preferably 7 g/l to 10 g/l. In terms of percentages by weight of gellan gum relative to the medium, the preferred concentration is preferably above 0.6%, normally 0.6 to 1.2%, more preferably above 0.8%, and normally about 1.0%. The conventional concentration of gellan gum used in growth media is typically about 0.1 to 0.4%, so it can be seen that the amount of gum used in the present invention is significantly higher.

With respect to agar (marketed under the names Noble@, MBI® and Difco-Bacto®, among others) the preferred concentration range is between 16 g/l to 20 g/l. It is preferred that the gel strength in the medium fall within the range of 500–1100 g/cm$^{-2}$, more preferably from 700–800 g/cm$^{-2}$. The applicants have found a significant positive response of the somatic embryos during development and maturation of embryogenic cultures, regardless of the basal medium used, to higher than expected levels of gelling agent.

The amount of gelling agent used in the growth medium depends to some extent on the gelling property of the particular agent. Agents with higher gelling strengths are usually required in lower concentrations. Normally, the required concentration of gelling agents is such that it results in a gel strength at least 135 g/cm$^{-2}$, more commonly 500–1400 g/cm$^2$, and most preferably 750–1400 g/cm$^2$.

By using gelling agents of increased concentrations as disclosed herein and in conjunction with media of water potential in the range of −0.43 to −0.44 MPa, we provide availability of water that is optimal for increasing mature somatic embryo numbers, quality and desiccation tolerance. The optimal water availability is defined by the water potential of the embryogenic tissue and mature somatic embryos. The range of useful tissue water potential is from −0.20 MPa to −1.20 MPa. (Details of how water potential can be measured are provided in Example 3 below).

Figure 1B:
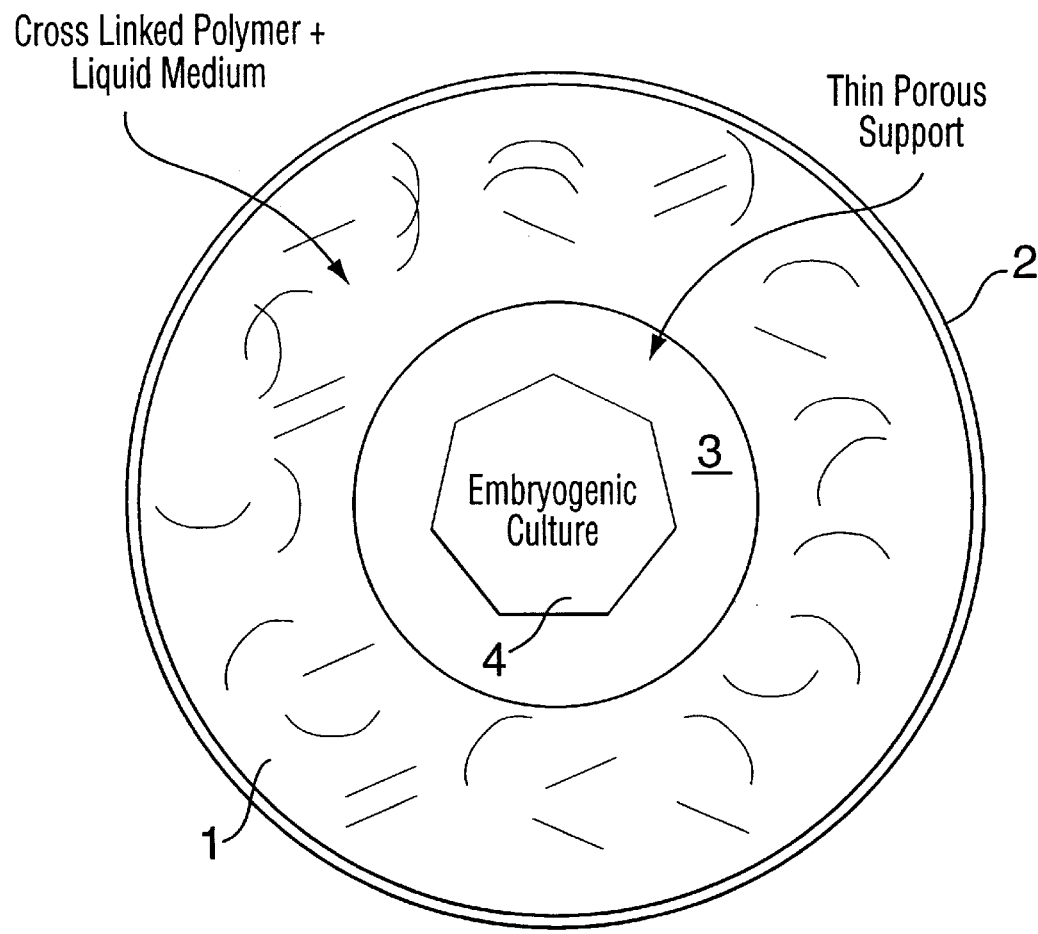

The present invention also provides a growth environment suitable for maturing somatic embryos wherein in the water potential of the environment is manipulated by adjusting the water availability within a substrate by adjusting only the concentration of the gelling agent. The nutrients necessary for embryo maturation are added in the form of liquid media at the concentrations known in the art to be appropriate for somatic embryo development, but their concentrations are not manipulated to affect the water potential of the substrate or of the embryogenic culture and/or somatic embryos. With reference to FIGS. 1A and 1B, molten cross-linked gel 1 is dispensed into a container 2 and allowed to solidify, after which a thin porous support 3 comprised of filter paper, filter pads, screens and the like, may be placed onto the cross-linked gel. It is onto the surface of the cross-linked gel or alternatively, onto the thin porous substrate laid on top of the gel, that the embryogenic culture 4 is placed and held during embryo maturation.

Australian Patent Application 37150/93 by Smith (hereinafter, the "Smith Application") discloses a very specific medium composition used for development, maturation and germination of embryogenic cultures, particularly for Pinus radiata, in which the solute concentration of the medium is altered. This alteration apparently allows maintenance of the embryogenic cultures without the need to add plant growth regulators such as auxins and cytokinins. Generally, the level of calcium is lower and the levels of total nitrogen, copper, zinc and sodium are increased. Disclosure is made of transiently increasing the gelling agent concentration in the medium in an early phase of maturation.

There are at least two key differences between the Smith Application and the present invention. Firstly, in the Smith Application, the gelling agent concentration is only transiently increased and is not maintained at this higher level for the duration of maturation. The culture is transferred from one medium with a higher concentration of gelling agent to a medium with a lower concentration of gelling agent, all during the maturation phase. With the method of the present invention, exposure to the higher level of gelling agent is continuous. Secondly, the maturation medium disclosed in the Smith Application are very specific in composition and use, as summarized above. In contrast, the method of the present invention contemplates that any media known in the art for maturing somatic embryos, may be manipulated by increasing the gelling agent concentration, to mature somatic embryos.

In another embodiment of the invention, the water potential of the embryogenic tissue and/or somatic embryos is effectively reduced by placing the embryogenic cultures on a porous support within a medium-containing vessel, wherein the support is positioned such that the somatic embryogenic culture is in contact only with medium that is incorporated within the structure of the physical support.

Figure 2:
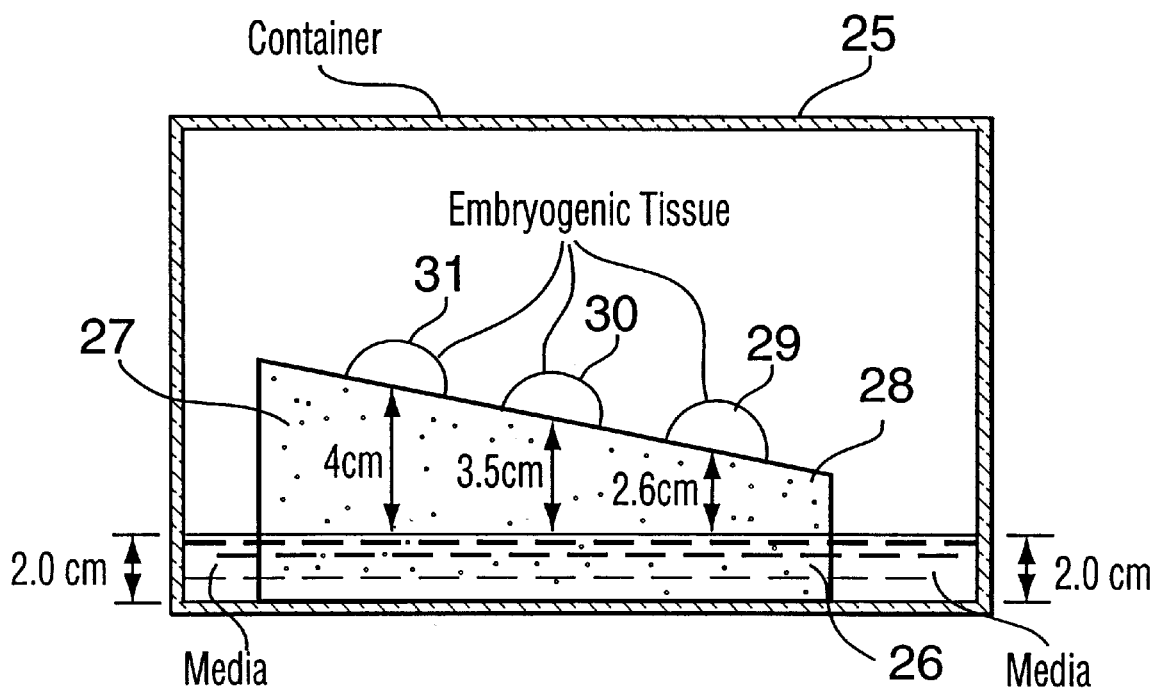
FIG. 2 is a schematic drawing showing one embodiment of a growth environment as contemplated within this invention, used to obtain the results shown in Example 5. The growth environment in this example comprises a porous support with a sloping upper surface that enables positioning embryogenic cultures at different heights above the liquid maturation medium, thereby affecting water availability to the cultures.

With reference to FIG. 2, which shows example of a suitable growth environment, culture vessel 25 is provided which may be any conventional petri dish or plate or other suitable container. Disposed within the vessel is a maturation medium 26. A porous support 27 fits within vessel 25 and is in direct contact with medium 26. However, at least one surface 28 of support 27 is separated from direct contact with medium 26. It is on surface 28 that embryogenic cultures are placed for embryo development and maturation. Furthermore, surface 28 of support 27 is provided with an angle such that one end of surface 28 is more elevated about medium 26 than the other end. Thus, the water availability to the embryogenic cultures can be manipulated by the locations on surface 28 where the cultures are placed. With reference to FIG. 2, embryogenic culture placed at location 29 is 2.6 cm from the surface of medium 26, while embryogenic culture placed at location 30 is 3.5 cm from the medium surface, and embryogenic culture placed at location 31 is 4.0 cm from the medium surface 26. Consequently, water availability to the cultures progressively decreases from location 29 to 30 to 31. The culture vessel is then sealed from the environment to provide sterile conditions and optionally, with a further sealing means covering the vessel and lid or cover such as a cling film of plastic material, adhesive tape or the like (not shown).

Figure 3:
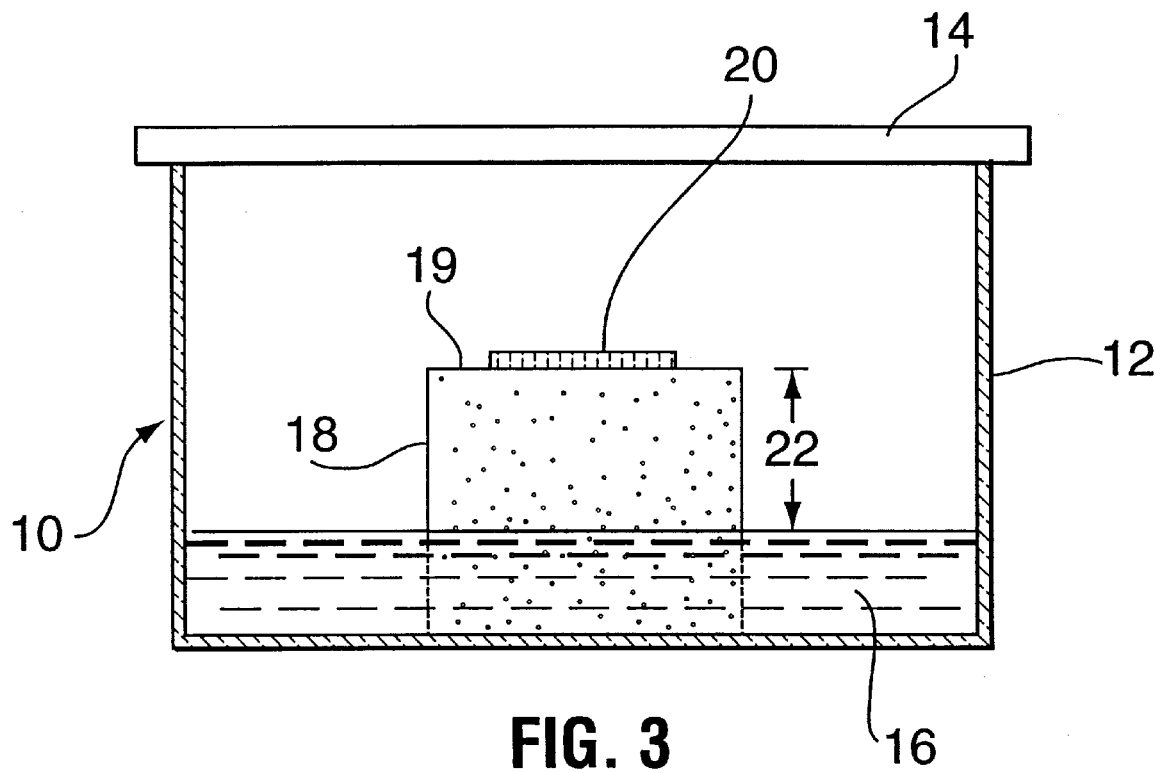
FIG. 3 is a schematic drawing showing one embodiment of a growth environment as contemplated within this invention, used to obtain the results shown in Example 6. The growth environment in this example comprises a porous support that enables positioning embryogenic cultures at a specific height above the liquid maturation medium. The availability of water to the cultures can be manipulated by adjusting the height of the porous support placed into the growth environment.

Another example of a suitable growth environment is illustrated in FIG. 3 which shows an example of a growth environment 10, a culture vessel 12 is provided which may be any conventional petri dish or plate or other suitable container, having a lid or cover 14. Disposed within the vessel is a maturation medium 16. A porous support 18 fits within vessel 12 and is in direct contact with medium 16. However, at least one surface 19 of support 18 is separated from direct contact with medium 16. It is on surface 19 that embryogenic culture 20 is placed during maturation.

In a preferred form and with reference to FIG. 3, liquid maturation medium 16 is placed within the culture vessel 12. Porous support 18 is then placed within culture vessel 12 at least partially in contact with the medium but such that one surface 19 of the support is elevated above and out of direct contact with the medium. The culture vessel is then sealed from the environment by lid 14 to provide sterile conditions and optionally, with a further sealing means covering the vessel and lid or cover such as a cling film of plastic material, adhesive tape or the like (not shown).

The degree of porosity of the material may be chosen according to the particular requirements of each maturation process. This may be readily determined without undue experimentation by a person skilled in this technical field.

Accordingly, any porous natural or synthetic material may be used which provides a gradient of water potential resulting from the height shown in FIG. 3 at 22 (distance between the surface holding the culture and the medium). It is preferred that the support comprise a natural or synthetic open-celled foam or sponge such as, but not restricted to polyurethane foams, e.g. Oasis™ foam, cellulose sponge or pads, pads of rock fibers, e.g. Rockwool™, or pads of fibres such as polyester, nylon, or cellulose. In addition, differential water-permeable membranes or filters may be used.

The appropriate height of the surface of the porous support holding the embryogenic culture is dependent upon the porosity and hence matric potential of the material used to make the support. As an example in the case of Oasis™ foam, it has been found that the preferred height which gives rise to good somatic embryo production by *Picea glauca* is in the range of 10–14 mm above the medium level. This will likely vary for other types of support material and other plant species.

In operation, the somatic embryo culture at the appropriate stage of development (refer to U.S. Pat. Nos. 5,238,835 and 5,563,061 for methods of preparing somatic embryos to the maturation phase, the disclosures of both of which are incorporated herein by reference) is placed on the surface of a porous support. This support may have been previously placed within a culture vessel such as petri dish or plate or other suitable container containing a culture medium, or it may be fitted within the vessel subsequent to the placement of the somatic embryo cultures thereon.

One principal advantage of this maturation method is that water availability in the culture can be precisely controlled without changing the solute composition and concentration, simply by selecting a physical support with certain porosity properties and/or by adjusting the height of the culture medium within the culture vessel. Accordingly, the resulting somatic embryos are of higher quality and show greater germination success rates than embryos produced using other maturation methods. In addition, using this method, the medium can be refreshed without removing the culture from the support. Furthermore, the water potential can be altered very simply by increasing or reducing the level of free liquid medium in the culture vessel, thereby altering the height of the surface of the support holding the culture above the medium. Heretofore, the separation of the somatic embryo culture from the medium by way of a porous support, the matrix of which carries water to and controls its availability to the embryogenic culture has not been contemplated for maturation phase of embryogenesis processes, nor have the attendant advantages been appreciated.

The methods disclosed herein are suitable for use with embryogenic tissue from any plant species without limitation. However, these methods may be used with embryogenic tissue from gymnosperm species, in particular from the gymnosperm plant families Araucaieaceae, Cupressaceae, Cycadaceae, Gingkoaceae, Pinaceae, and Taxaceae, and also, from angiosperm species, in particular from the angiosperm plant families Aceraceae, Fagaceae, Hamamelidaceae, Leguminoseae, Myrtaceae, Rosaceae, and Salicaceae, and hybrids thereof.

The present invention also provides a growth environment suitable for maturing somatic embryos wherein the water potential of the embryogenic tissue is configured to optimize embryo development and maturation. The growth environment, as discussed in more detail above with respect to the method of operation, comprises, with reference to FIG. 3, culture vessel 12 comprising maturation medium 16 and porous support 18 which is placed with vessel 12 such that surface 19 of the support is separated from direct contact with medium 16. It is on surface 19 that embryogenic culture 20 is held during maturation.

The somatic embryos, matured in accordance with the present invention, may be dried by the methods and techniques disclosed in the McKersie Patent (see background section above) or in PCT Patent Application No. 91/01629 and published on Feb. 21, 1991 (hereinafter, the "BCRI Patent"), the contents of both of which are incorporated herein fully by reference. The McKersie Patent discloses two types of embryo drying techniques: fast drying which is achieved by air drying or in a low relative humidity chamber. Under this regimen, embryos are dried to as low as 7.4% moisture content within a day. Slow drying is achieved by placing the embryos in a series of desiccators with controlled relative humidity for six days. For the first day of drying, embryos are kept at 97% humidity and are transferred daily in succession to chambers with 87%, 75.7%, 62.55%, 50.5% and finally to 43% humidity.

The BCRI Patent discloses partial drying wherein the embryos are exposed to an atmosphere having a relative humidity of between 85–99.9% prior to germination for at least one day.

Accordingly, using the methods disclosed herein and the drying methods incorporated by reference, matured, dried somatic embryos are produced having superior germination frequencies and moisture contents which approximate those of natural zygotic seeds.

EXAMPLE 1

MATURATION OF *Pinus strobus* SOMATIC EMBRYOS ON MEDIA WITH ELEVATED LEVEL OF GELLAN GUM Three media, MSG (Becwar et al. 1990), ½ LM medium (Litvay et al. 1985) with macroelements reduced to half-strength, and EMM medium (Smith 1994) were used in the experiments. MSG and ½ LM contained 40 mg $l^{-1}$ iron chelate (7%, Plant Products, Brampton, Ontario, Canada) as iron source. The pH of the media was adjusted to 5.8 prior to sterilization in the autoclave (121° C., 1.25 kg $cm^{-2}$, 18 min.). The amino acid solutions were filter-sterilized and mixed into the cooled media. MSG medium was supplemented with 1.46 $gl^1$L-glutamine, ½ LM with 0.5 $gl^{-1}$ L-glutamine and 1 $gl^{-1}$ casein hydrolysate (CH, Sigma)

Maturation experiments were carried out within a period of 8 months with five embryogenic lines of *Pinus strobus* identified as wp-94-5 and wp-94-7 (both wp-94- lines were maintained in culture for 15 months since initiation) and wp-95-6a, wp-95-7a, and wp-95-9a (the wp-95- lines were maintained in culture for 8 months since initiation).

The somatic embryo maturation experiments were performed by combining embryogenic tissue of one line (from several plates), one week after subculture, in a 50-ml test tube, adding liquid medium without growth regulators and vigorously shaking the tube to break up the clumps of tissue into a fine suspension. Subsequently, 3 ml containing 0.3 or 0.5 g of the suspended embryonal mass were withdrawn with the wide-mouth pipette and placed on the moist filter paper disc (Whatman #2, 5.5 cm in diameter) in Buchner funnel attached to a vacuum pump. A short, low-pressure pulse (5 sec, −4.6 kPa) was applied to remove all the liquid medium and anchor the embryonal mass to the filter paper as a thin layer. Each disc of filter paper with the embryonal mass was subsequently placed on a maturation medium in 10 mm×20 mm Petri dishes and cultured for up to 10 weeks. The cultures were kept under dim light condition at 1.6 $\mu$mol $m^{-2}$ $s^{-1}$ from cool white fluorescence lamps (Philips F72T12/CW. 56 Watt) under a 16-h photoperiod at 24±° C.

Three maturation media formulations (½ LM, ½ LMaa, MSG and EMM; each containing ABA, 3% sucrose, and gellan gum (Phytagel™, Sigma lot # 83H0854) were prepared in 450-ml aliquots. In ½ LMaa, all the components were the same as in ½ LM except for the organic additives; glutamine (0.5 g $l^1$) and CH (1.0 gl $^1$) were replaced by amino acid mixture (Smith 1994): glutamine 7.3 $gl^{-1}$ asparagine 2.1 $gl^{-1}$, arginine 0.7 $gl^{-1}$, citrulline 0.079 $gl^{-1}$, omithine 0.076 $gl^{-1}$, lysine 0.0559 $gl^{-1}$ alanine 0.04 $gl^{-1}$, and proline 0.035 $gl^{-1}$. EMM medium was prepared as described in Smith (1994) The pH of the media was adjusted to 5.8 prior to sterilization in the autoclave. The solutions of amino acids and ABA were pH adjusted to 5.8, filter sterilized and added in 50-ml aliquots to the sterile, warm, media. Twenty five ml of the molten media were dispensed to each petri dish (100 mm×15 mm) and left unsealed to solidify in an active laminar air flow unit for 1 day.

Measurements of the gel strengths of the various media were carried out after 1 day after dispensing the media into petri dishes. For each time point, 3 petri dishes were tested.

Gel strength was measured with the TA.XT2 Texture Analyzer (Texture Technologies Corp., Scarsdale, N.Y., USA/ Stable Micro Systems, Godalming, Surrey, UK) using a 1.2-cm diameter cylinder probe (acrylic), trigger force 2 g, measured medium depth 2 mm, probe speed 1 mm s$^{-1}$, and pre/post test speed ⅔ mm s$^{-1}$. Since there was little variation in readings due to position, the readings were subsequently taken at the center of the petri dish. The gel strength of different media is presented as a ratio correlated to the ½ LM IM medium, used for initiation and maintenance of embryogenic cultures, which contains 0.4% gellan gum, 2% sucrose, 9.5 $\mu$M 2,4-D, and 4.5 $\mu$M BA.

Simultaneously, experiments on the somatic embryo maturation of lines wp-94-7 and wp95-6a were carried out using 1-day-old media. Three petri dishes were used for each maturation treatment. The number of cotyledonary somatic embryos was scored after 7, 8, and 10 weeks, and the embryos were transferred onto germination medium. Cotyledonary somatic embryos were placed horizontally on the surface of ½ LM medium containing 0.06 M sucrose and 0.6% gellan gum without growth regulators. The cultures were kept for two weeks under dim light (1.6 $\mu$mol m$^{-2}$s$^{-1}$), 16 h photoperiod, 24±° C. and then transferred to the higher light intensity (47 $\mu$mol m$^{-2}$s$^{-1}$) with the other physical conditions remaining as described. The germinants which displayed elongation of the cotyledons and roots (after 6–8 weeks) were inserted (with the roots down) into fresh medium of the same composition in 7 cm×10 cm magenta boxes (Sigma) containing 40 ml of medium and kept under conditions described above.

Somatic plants that showed epicotyl and root growth were planted in peat: vermiculite (3:1) mix and maintained in a growth chamber under controlled environmental conditions (16 h photoperiod, 20/1° C. day/night temperature, light intensity 170 $\mu$mol m$^{-2}$ s$^{-1}$ provided by fluorescent and incandescent lamps). The plants were fertilized twice per week with 100 ppm N applied as 20:20:20 N:P:K (Plant Products, Brampton, Ontario, Canada).

Media were solidified with various concentrations of gellan gum, and the gel strengths were measured and related to the gel strength of ½ LM IM medium designated by 1.0 (Table 1). As expected, the relative gel strengths were positively correlated to the concentration of gellan gum in the medium. Media containing relatively high concentrations of the solidifying agent appeared to be "dryer" thane media which contained lower concentrations of the solidifying agent and consequently, would have less "free" water available for uptake by embryogenic tissues developing somatic embryos. In general, gellan gum at 0.4 and 0.6% formed gels with strength that varied depending on the medium basal salt composition (Table 1). For example, 0.4% gellan gum in ½ LM IM medium resulted in the formation of softer gel than in MSG IM medium, and large differences in gel strength were noted when 0.6% gellan gum was used to solidify ½ LM versus EMM medium.

On the other hand, when gellan gum was used at 1% in ½ LM, ½ LM and MSG media, the difference in gel strength readings were negligible (4.3, 4.2, 4.4, respectively) indicating that at this concentration neither basal salts nor organic nitrogen composition had an effect on the tested gel property.

To evaluate the effect of gellan gum concentration (gel strength) on the development of somatic embryos, the maturation experiment was carried out with two embryogenic lines on the media prepared for the gel strength tests, all containing 3% sucrose and 80 $\mu$M ABA (Table 1). The growth of the cultures and the development of the mature embryonal structures strongly depended upon the gel strength and was not influenced by the organic nitrogen composition (see ½ LM versus ½ LMaa). A clear trend was observed in the tissue proliferation rate of the cultures that ranged from relatively abundant on media with relative gel strength of 0.4–1.3 to moderate on 1.8–2.3 gels and minimal on 3.2–5.1 gels. Upon microscopic examination it was noted that the abundant growth was mainly confined to the suspensor-type cells and callusing of the precotyledonary somatic embryos. Media with high-gel strength supported mainly growth of somatic embryos and maturation . The number of mature somatic embryos was positively correlated to the relative gel strength. However, the two tested lines showed different responses on the corresponding media; line wp95-6a produced mature somatic embryos on most of the tested media whereas line wp-94-7 produced them only on media with gel strength ranging between 3.2 to 5.1. The mature somatic embryos on media with low gel strength (0.7–1.3) were approximately 3 mm in length and those on media with harder gels were slightly shorter (approximately 2.0 mm). Most of the somatic embryos matured after 7 to 10 weeks of culture.

Cotyledonary somatic embryos of line wp95-6a from all the tested ½ LM and ½60 LMaa media were germinated. Of 538 somatic embryos, 347 (64%) displayed elongation of the cotyledons and hypocotyl and growth of the primary root. The germination frequencies for ½ LM 0.4, 0.6, 0.8, 1.0, and 1.2% gellan gum were 58, 44, 61, 70, 78%, and for ½ LMaa 0.45, 0.6, and 1.0% gellan gum they were 50, 55, and 79% respectively. These results indicated that embryos derived from high gel strength had improved conversion frequencies.

TABLE 1

Relative medium gel strength of different maturation media solidified with gellan gum at various concentrations, calculated relative to the ½ LM IM medium with 0.4% gellan gum (1.0) and the maturation response of *P. strobus* somatic embryos. Three hundred mg fresh weight of embryogenic tissue were anchored to the filter paper disc per each of the 3 petri dishes per treatment. Relative gel strengths of the media were measured 1 day after dispensing into the petri dishes.

| Medium and supplements | Gellan gum (%) | Relative gel strength* | No. of cotyledonary somatic embryos g$^{-1}$ FW embryogenic tissue* | |
|---|---|---|---|---|
| | | | wp-95-6a | wp-94-7 |
| ½ LM IM | 0.4 | 1.0 (0.05) | — | — |
| MSG IM | 0.4 | 1.5 (0.02) | — | — |

TABLE 1-continued

Relative medium gel strength of different maturation media solidified with gellan gum at various concentrations, calculated relative to the ½ LM IM medium with 0.4% gellan gum (1.0) and the maturation response of P. strobus somatic embryos. Three hundred mg fresh weight of embryogenic tissue were anchored to the filter paper disc per each of the 3 petri dishes per treatment. Relative gel strengths of the media were measured 1 day after dispensing into the petri dishes.

| Medium and supplements | Gellan gum (%) | Relative gel strength* | No. of cotyledonary somatic embryos $g^{-1}$ FW embryogenic tissue* | |
|---|---|---|---|---|
| | | | wp-95-6a | wp-94-7 |
| ½ LM 3% sucrose + 80 μM ABA | 0.4 | 1.3 (0.03) | 53 (35) | 0 |
| ½ LM 3% sucrose + 80 μM ABA | 0.6 | 2.3 (0.05) | 155 (114) | 0 |
| ½ LM 3% sucrose + 80 μM ABA | 0.8 | 3.2 (0.32) | 180 (32) | 30 (3) |
| ½ LM 3% sucrose + 80 μM ABA | 1.0 | 4.3 (0.09) | 280 (74) | 108 (45) |
| ½ LM 3% sucrose + 80 μM ABA | 1.2 | 5.1 (0.14) | 295 (45) | 77 (10) |
| ½ LM aa 3% sucrose + 80 μM ABA | 0.45 | 1.1 (0.06) | 61 (22) | nt |
| ½ LM aa 3% sucrose + 80 μM ABA | 0.6 | 1.8 (0.07) | 78 (11) | nt |
| ½ LM aa 3% sucrose + 80 μM ABA | 1.0 | 4.2 (0.09) | 255 (106) | nt |
| EMM 3% sucrose + 80 μM ABA | 0.45 | 0.4 (0.04) | 0 | 0 |
| EMM 3% sucrose + 80 μM ABA | 0.6 | 0.7 (0.04) | 15 (15) | 0 |
| MSG 3% sucrose + 80 μM ABA | 1.0 | 4.4 (0.14) | nt | nt |

* Numbers are means (±SD) of 3 replicates
nt- not tested.

EXAMPLE 2

SOMATIC EMBRYO DEVELOPMENT ON MEDIA WITH VARIED GELLAN GUM CONTENT AND ABA CONCENTRATIONS, AND ON MEDIA CONTAINING PEG:

A further series of experiments was carried out with four embryogenic lines of Pinus strobus on ½ LM medium with 3% sucrose, various concentrations of gellan gum and ABA (Table 2). The results showed a similar trend as in Example 1 with high mean numbers of cotyledonary somatic embryos observed on media with 1% gellan gum. Interestingly, the results also showed beneficial effect of increased ABA content in the media on the embryo development. At the given concentration of gellan gum, supplementing the medium with progressively higher concentration of ABA resulted in higher numbers of mature somatic embryos with the exception of 1.2% gellan gum where the trend was not as clear. The only line tested on medium with 1% gellan gum but without ABA also produced mature somatic embryos however the number was substantially lower than on the corresponding media with ABA (Tables 1 and 2).

Radicle emergence and growth of the germinants was affected by the maturation medium used to produce the somatic embryos, with variations in the gellan gum concentrations having more pronounced effects than the changes in ABA concentrations. Somatic embryos that matured on media with 1% gellan gum showed higher incidence of germinants with roots than those derived from media with lower concentration of gellan gum (data not shown).

Another experiment was conducted to compare maturation medium with high concentrations of gellan gum with media containing PEG as a non-permeating osmoticum. Medium supplemented with PEG was gelled with a standard concentration of gellan gum (0.4%) to enable assessment of PEG as an osmoticum versus the physical method of controlling water availability by increasing the gellan gum concentration of the medium. More somatic embryos were produced on medium containing 0.4% gellan gum plus PEG than were produced on medium containing 0.4% gellan gum but no PEG (Table 3). However, media containing elevated gellan gum concentrations produced more somatic embryos than the PEG-amended medium. Furthermore, somatic embryos produced on PEG-amended medium did not produce normal germinants while those produced on media containing 0.8% and 1.0% gellan gum concentrations demonstrated 55% and 95% germination success, respectively (Table 3).

TABLE 2

Maturation and germination of P. strobus somatic embryos on ½ LM medium with 3% sucrose and different gellan gum and ABA concentrations. The means (±SD) were combined for all 4 lines tested; wp-94-5, wp-94-7, wp-95-7a, and wp-95-9a. Three experiments with each line and 3 replicates per each treatment were carried out.

| Gellan gum (%), ABA (μM) | Mean number of mature somatic embryos $g^{-1}$ FW embryogenic tissue | No. of somatic embryos germinated/No. of somatic embryos tested |
|---|---|---|
| 0.45, 80 | 0 | — |
| 0.6, 40 | 4 (4.0) | Nt |
| 0.6, 60 | 2 (2.8) | Nt |
| 0.6, 80 | 7 (8.5) | 0/10 |
| 0.6, 120 | 17 (24) | 5/20 |
| 0.8, 80 | 30 (28) | 25/42 |

TABLE 2-continued

Maturation and germination of *P. strobus* somatic embryos on ½ LM medium with 3% sucrose and different gellan gum and ABA concentrations. The means (±SD) were combined for all 4 lines tested; wp-94-5, wp-94-7, wp-95-7a, and wp-95-9a. Three experiments with each line and 3 replicates per each treatment were carried out.

| Gellan gum (%), ABA (μM) | Mean number of mature somatic embryos $g^{-1}$ FW embryogenic tissue | No. of somatic embryos germinated/No. of somatic embryos tested |
| --- | --- | --- |
| 0.8, 120 | 59 (45) | 21/44 |
| 1.0, 0 | 13 (6)* | Nt |
| 1.0, 40 | 30 (28) | Nt |
| 1.0, 60 | 37 (21) | Nt |
| 1.0, 80 | 68 (64) | 35/44 |
| 1.0, 120 | 138 (54) | 39/57 |
| 1.2, 40 | 18 (7) | Nt |
| 1.2, 60 | 22 (4) | Nt |
| 1.2, 80 | 28 (20) | Nt |

\* Only line wp-95-6a was tested.
nt - not tested.
Numbers in brackets are S.D.

TABLE 3

Maturation of somatic embryos of eastern white pine (*Pinus strobus*, line 6a) after 9 weeks on ½ LM medium with 3% sucrose, 120 μM ABA, PEG and several concentrations of gellan gum (Phytagel ™)

| Gellan gum (%), PEG (%) | No. of mature somatic embryos $g^{-1}$ FW tissue | Germination (%) |
| --- | --- | --- |
| 0.4 gellan gum, 7.5 PEG | 155 ± 65 | 0* |
| 0.4 gellan gum | 0–10 | n/a** |
| 0.8 gellan gum | 250 ± 90 | 55 |
| 1.0 gellan gum | 410 ± 35 | 95 |

\* No germinants with normal morphology, all the germinants had red, thick hypocotyls, short roots and cotyledons and some of them had split epidermis.
\*\* n/a - not available

EXAMPLE 3

MATURATION OF *Pinus strobus* SOMATIC EMBRYOS ON MEDIUM COMPRISING FOUR SELECTED TYPES OF GELLING AGENTS AND THE WATER POTENTIAL OF EMBRYOGENIC TISSUE AND SOMATIC EMBRYOS MATURED ON MEDIUM SOLIDIFIED WITH GELLAN GUM.

Gellan gum is prepared from a bacterial (*Pseudomonas elodea*) polysaccharide which is composed of glucuronic acid, rhamnose and glucose, and as such, differs from other tissue culture media solidifying agents such as agars. Agars are derived from the sea weeds (agarophytes) and represent a spectrum of closely related polysaccharides belonging to the family of galactans. Furthermore, multi-lement analyses of gellan gum (Gelrite, K9A 40, Kelco, USA) and agar (purified, Merck) revealed quantitative and qualitative differences in their inorganic fraction (Sherer et al. 1988). These quantitative and qualitative differences between the two gelling agent types are significant enough to pose a question concerning the possibility of stimulatory effect of certain gellan gum components on the maturation of somatic embryos of *P. strobus*. To determine if this was a viable hypothesis, *P. strobus* somatic embryo maturation was carried out on media gelled with several types of agars and gellan gum. In order to make the comparison meaningful, gel strengths of all the maturation media were measured and the growth of embryonal masses compared at similar gel strength values on the different types of gelling substrates. Moreover, a simple technique was used to determine the amount of liquid available from the medium to the plated embryogenic tissue at the onset of maturation.

Subsequently, we also investigated if exposure of embryogenic tissues and somatic embryos to different amounts of liquid medium would affect their, i.e., the cultures' and somatic embryos', water potential. First, we measured the water potentials of the different maturation media solidified with various concentrations of gellan gum. Subsequently, we measured the water potentials of the embryogenic tissue and somatic embryos at various time points during the culture periods on the different maturation media.

*P. strobus* embryogenic culture of line 95-6a was maintained for two years prior to the maturation experiments by biweekly subcultures onto modified Litvay's medium (½ LM, see above) (Litvay et al. 1985) containing 1 $gl^{-1}$ casein hydrolysate, 0.5 $gl^{-1}$ L-glutamine, 9.5 μM 2,4-D, 4.5 μM BA, 2% sucrose and 0.4% gellan gum (Phytagel™, Sigma). For the maturation experiments, the tissue was bulked up, collected and plated on the filter papers (Whatman #2, 5.5 cm disc) as previously described (see Example 1). The maturation medium was ½ LM as above except for 3% sucrose and ABA at 80 μM (filter sterilized) as a sole growth regulator, pH 5.8. The cultures were kept at 230±2° C., low light intensity (cool white, fluorescence tubes) 16 h photoperiod for nine weeks prior to scoring the number of mature somatic embryos.

Gellan gum (Phytagel™, Sigma) was tested at 0.4, 0.6, 0.8, 1.0 and 1.2% (w/v). Agars Difco-Bacto® and Difco-Noble® were tested at 0.8, 1.6, 2.0, 2.4 and 2.8% (w/v). Agars MBI #1 and #2 derived from cloned algae and obtained from Marine BioProducts International Corp. (Vancouver, BC, Canada) were tested at 0.6, 1.0, 1.5, 2.0% and 1.0, 1.5, 2.0. 2.5% (w/v) respectively. The latter agars, #1 and #2 differed with respect to the gelling property (gel strength).

The maturation medium was supplemented with various gelling agents, autoclaved at 121° C., 0.12 MPa for 18 min in 250-ml aliquots. After addition of the filter-sterilized solution of L-glutamine and ABA, the medium was dispensed at 25 ml per Petri dish and allowed to cool in the active, vertical flow laminar hood for 24 h. Three Petri dishes per each of the maturation media were used for measurements of the gel strength 48 h after dispensing. The measurements were taken in the center of the Petri dish using MT-Micro materials tester, (Stable Micro Systems, Surrey, England), probe size 1 cm$^2$, trigger force 2 g, measured medium depth 2 mm.

Simultaneously the availability of liquid in the maturation media solidified with gellan gum, agar Difco-Noble® and agar MBI #1 at various concentrations were determined by placing the autoclaved, pre-weighed filter paper discs (Whatman # 2, 5.5 cm) on the surface of the medium. The plates were sealed with Parafilm™ and incubated for 48 h under the same conditions as the embryogenic cultures for maturation of somatic embryos. The filter papers were subsequently weighed and the amount of retained liquid was determined in six Petri dishes per tested medium.

Water potentials of maturation media solidified with various concentrations of gellan gum were measured using a Vapor Pressure Osmometer model 5520 (Wescor, Inc., Utah, USA) according to the protocol outlined in the User's Manual. Briefly, the sample discs (3 per petri dish) were placed on the surface of the gelled medium in the petri dishes. The plates were sealed with Parafilm™ and left for several hours (i.e., from 2 to 24 hrs). No differences were noted in the water potentials of the media after the different equilibration times of the sample discs. The water potential of each sample disc was determined by placing it into the sealed sample chamber (AC-063) for 3 min prior to initiating the measurement cycle. The osmolality unit (mmol/kg) recorded by the machine was subsequently converted to the water potential unit MPa at 25° C.

Twenty to 30 somatic embryos were collected from each maturation medium after 9 weeks and placed on ½ LM medium with 2% sucrose and 0.4% gellan gum in 100×15 mm Petri dishes for germination. The cultures were placed under low light intensity (cool white, fluorescence tubes), 16 h photoperiod. The embryos were scored as germinated if the radicle length was at least 3 mm and the hypocotyl and cotyledons were green and elongated.

Water potentials of embryogenic tissues and somatic embryos were measured with the Vapor Pressure Osmometer model 5520 (Wescor, Inc., Utah, USA) using a larger sample holder (part # AC-064) according to the protocol in the User's Manual for measuring the water potential of large samples. The embryogenic tissue (approximately 20–30 mg fresh mass) or somatic embryos (7 to 12, depending on the size) were collected at various time points during maturation periods on the different maturation media. The samples were placed as quickly as possible in the sample chamber, which was then quickly sealed and left first for 5 min prior to initializing the measurement cycle. After recording the first value, the sample was left in the sample chamber for the next 3 minutes or multiples of the 3 minute period until the consecutive values recorded differed by less than 10 mmol/kg. The osmolality units (mmol/kg) were subsequently converted to the water potential unit MPa at 25° C.

Gel strength in the different media was dependent on the concentration of solidifying agents. Compared to agars, gellan gum formed gels of the highest strength when used at the same concentration (Table 4). For example, to form gel that was similar in strength to 0.8% gellan gum, it was necessary to use approximately 2% of agar Difco-Bacto™ and Dicfo-Noble™, 1.4% agar MBI # 1 and 1.7 % agar MBI # 2.

The numbers of mature somatic embryos were positively correlated to the gel strength of the maturation media and did not depend on the type of gelling agent used (Table 4). This upward trend in the number of mature somatic embryos was observed on all the maturation media within the range of the gelling agent concentrations tested. Furthermore, the amount of proliferated tissue was visibly diminished on all media with higher gel strength which indicated that these media did not support tissue proliferation but only somatic embryo development. On media with gel strength approximately 800 g cm$^{-2}$ and greater (up to 1300 g cm$^{-2}$), most of the embryos reached cotyledonary stage after 9 weeks. However, many younger embryos were still observed. These somatic embryos developed further if left on the medium for a further two to three weeks. All the somatic embryos could be left, if necessary, on the same medium for up to 16 weeks and after becoming cotyledonary, most of them remained developmentally arrested. No greening or germination was noticeable on these media. Contrary to this, media of gel strength below 500 g cm$^{-2}$ not only produced fewer mature somatic embryos, but also, some of those embryos became green and showed elongation of the hypocotyl and radicle if left on the medium longer than eight to nine weeks. It is noteworthy that these somatic embryos were developing on the surface of the embryogenic tissue which initially proliferated abundantly, but after five to six weeks, became necrotic.

To test if the solidifying agents used at different concentrations would affect the availability of liquid from the gelled medium to the embryonal masses cultured on the surface of the filter paper, the change in the filter paper weight after incubation on the surface of medium was measured. Three solidifying agents were chosen for this test; gellan gum, agar Difco-Noble™ and agar MBI#1 (Table 5). The mean amount of liquid in the filter papers showed clear negative correlation to the gelling agent concentration. The difference in the amount of liquid present in the filter paper between the lowest (0.4%) and the highest (1.2%) gellan gum concentration was approximately 44 mg. For agar Difco-Noble™, the difference between 0.8 and 2.8% was 73 mg and for agar MBI #1 between 0.6 and 2.0%, it was 48 mg of liquid. Clearly, the embryogenic tissue cultured on the surface of filter papers was exposed to varying amounts of liquid at the onset of the culture. It is worthwhile to note that the liquid content in the filter papers was similar when compared among media of similar gel strength but gelled with different gelling agents (Table 5). Gels of similar strength values were formed by 0.8% gellan gum, 2.0% agar Difco-Noble and 1.4% agar MBI #1 (estimated) resulting in approximately 350 mg of liquid per filter paper.

There were similarities in the number of mature somatic embryos and germination frequency among the tested gelling agents if applied to give a similar medium gel strength and water availability. Therefore, it is concluded that the amount of water available to the embryogenic cultures placed on the maturation medium was a critical factor involved in the development of somatic embryos of *P. strobus*.

The water availability from the maturation medium had a significant effect on the water potential of the embryogenic tissue which in turn triggered and/or maintained the maturation process (Table 6). After one week of culture, the embryogenic tissue water potential was the same on all the tested media regardless of the gellan gum concentration and it was in an equilibrium with the water potential of the medium. All media solidified with 0.4 to 1.0% gellan gum had water potential of −0.43±0.01 MPa. Two weeks after the embryogenic cultures were placed on the media, trends in the changes of the water potentials within the embryogenic tissues cultured on various media became obvious. The embryogenic tissue cultured on media with 0.4 and 0.6% gellan gum had higher (less reduced) water potential than embryogenic tissue cultured on media with 0.8 and 1.0% gellan gum. This trend in the tissue water potential was maintained through week 4 of the culture. At week 6/7 mature somatic embryos developed on medium with 0.4 and 0.6% gellan gum and their water potential either remained the same as of the embryogenic tissue at week 4 (for 0.6% gellan gum) or increased, particularly on medium with 0.4% gellan gum. At this time, the somatic embryos developing on medium with 0.8 and 1.0% gellan gum were not yet mature (most were precotyledonary). At week 8/9, the somatic embryos on media with 0.4 and 0.6% gellan gum began to germinate or became hyperhydric while on media with 0.8 and 1.0% gellan gum, the somatic embryos reached cotyledonary stage. The water potentials of these mature somatic embryos were much lower than those which matured on media with lower concentrations of gellan gum. These low water potentials within somatic embryos on medium with 0.8 and 1.0% gellan gum were maintained through week 10 and 12.

TABLE 4

Maturation and germination response of *Pinus strobus* somatic embryos on ½-LM medium with 3% sucrose, 80 µM ABA and solidified with several concentrations of various gelling agents. Two hundred mg FW tissue were anchored to the filter paper disc for each of the 3 petri dishes per treatment. Numbers are means ± SD.

| Gelling agent (%) | Gel strength (g cm$^{-2}$) | Number of somatic embryos g$^{-1}$ FW tissue | Germination (%) |
|---|---|---|---|
| Gellan gum PHYTAGEL ™ | | | |
| 0.4 | 317 ± 18 | 65 ± 20 | nt |
| 0.6 | 501 ± 7 | nt | nt |
| 0.8 | 767 ± 44 | 160 ± 15 | 88 |
| 1.0 | 1072 ± 75 | 315 ± 60 | 92 |
| Agar Difco-Bacto ™ | | | |
| 0.8 | 135 ± 2 | 55 ± 35 | nt |
| 1.6 | 552 ± 22 | 220 ± 115 | 39 |
| 2.0 | 806 ± 34 | 320 ± 70 | 85 |
| 2.4 | 982 ± 3 | nt | nt |
| 2.8 | 1277 ± 17 | nt | nt |
| Agar Difco-Noble ™ | | | |
| 0.8 | 143 ± 1 | 2.5 ± 3.5 | nt |
| 1.6 | 569 ± 8 | 170 ± 40 | 100 |
| 2.0 | 750 ± 81 | 290 ± 40 | 85 |
| 2.4 | 986 ± 3 | nt | nt |
| 2.8 | 1345 ± 7 | nt | nt |
| Agar MBI-1 | | | |
| 0.6 | 183 ± 5 | 0.5 ± 0.7 | nt |
| 1.0 | 437 ± 16 | 16 ± 3 | 90 |
| 1.5 | 842 ± 36 | 28 ± 3 | 86 |
| 2.0 | 1330 ± 44 | 45 ± 14 | 89 |

TABLE 4-continued

Maturation and germination response of *Pinus strobus* somatic embryos on ½-LM medium with 3% sucrose, 80 µM ABA and solidified with several concentrations of various gelling agents. Two hundred mg FW tissue were anchored to the filter paper disc for each of the 3 petri dishes per treatment. Numbers are means ± SD.

| Gelling agent (%) | Gel strength (g cm$^{-2}$) | Number of somatic embryos g$^{-1}$ FW tissue | Germination (%) |
|---|---|---|---|
| Agar MBI-2 | | | |
| 1.0 | 265 ± 10 | 30 ± 20 | nt |
| 1.5 | 565 ± 28 | 105 ± 15 | 90 |
| 2.0 | 937 ± 15 | 250 ± 15 | 91 |
| 2.5 | 1323 ± 21 | 210 ± 25 | 95 | nt - not tested

TABLE 5

Liquid content in the filter paper discs placed (for 48 h) on the surface of ½ LM medium with 3% sucrose, 80 µM ABA and solidified with several concentrations of selected gelling agents and the maturation response and germination frequency of *Pinus strobus* somatic embryos. Two hundred mg FW of tissue was anchored to the filter paper disc for each of the 3 petri dishes per treatment.

| Gelling agent (%) | Liquid content in 227 mg filter paper (mg) | No of somatic embryos g$^{-1}$ FW tissue | Germination (%) |
|---|---|---|---|
| Gellan gum (Phytagel ™) | | | |
| 0.4 | 367.8 ± 6.9 | 30 ± 14 | nt |
| 0.6 | 355.0 ± 5.8 | 85 ± 42 | 30 |
| 0.8 | 352.8 ± 7.5 | 112 ± 32 | 70 |
| 1.0 | 336.2 ± 3.9 | 300 ± 65 | 65 |
| 1.2 | 323.4 ± 5.3 | 475 ± 205 | nt |
| Agar Difco-Noble ™ | | | |
| 0.8 | 385.4 ± 5.1 | 17 ± 3.5 | nt |
| 1.6 | 362.4 ± 4.9 | 252 ± 45 | 40 |
| 2.0 | 344.5 ± 7.3 | 370 ± 10 | 65 |
| 2.4 | 322.7 ± 5.4 | 260 ± 42 | 70 |
| 2.8 | 312.3 ± 7.6 | 262 ± 45 | 75 |
| Agar MBI #1 | | | |
| 0.6 | 378.0 ± 13.0 | 0 | nt |
| 1.0 | 371.6 ± 8.8 | 22 ± 25 | nt |
| 1.5 | 339.0 ± 3.2 | 142 ± 60 | 44 |
| 2.0 | 330.4 ± 15.8 | 160 ± 7 | 53 |

Numbers are means ± SD
nt - not tested

TABLE 6

Water availability of *Pinus strobus* (line 6a) embryogenic cultures and somatic embryos on ½ LM maturation medium with 3% sucrose, 120 μM ABA and various concentrations of gellan gum (Phytagel ™).

Water potential (MPa)

| Gellan gum (%) | 1 wk | 2 wks | 4 wks | 6/7 wks | 8/9 wks | 10 wks | 12 wks |
|---|---|---|---|---|---|---|---|
| 0.4 | −0.44 ± 0.01 | −0.37 ± 0.03 | −0.39 ± 0.04 | −0.26 ± 0.04 | precocious | n/a | n/a |
| 0.6 | nt | −0.33 ± 0.04 | −0.32 ± 0.05 | −0.32 ± 0.02 | precocious | n/a | n/a |
| 0.8 | nt | −0.43 ± 0.01 | −0.45 ± 0.04 | not matured | −0.5 ± 0.02 | −0.54 ± 0.08 | −0.55 ± 0.06 |
| 1.0 | −0.45 ± 0.01 | −0.44 ± 0.03 | −0.47 ± 0.02 | not matured | −0.66 ± 0.06 | −0.67 ± 0.06 | −0.70 ± 0.00 |

Note: From 1 to 4 wks the water potential measurements were made on embryogenic tissue plus developing somatic embryos. From week 6, the water potentials were determined in somatic embryos only.
nt - not tested
n/a - not available

EXAMPLE 4

MATURATION OF CONIFER SOMATIC EMBRYOS (other than *Pinus strobus*) ON MEDIUM (½ LM) COMPRISING DIFFERENT CONCENTRATIONS OF GELLING AGENT, PEG AND ABSCISIC ACID (ABA) AND WATER POTENTIAL OF THE EMBRYOGENIC TISSUE AND SOMATIC EMBRYOS.

From the previous three examples it is evident that using maturation medium with increased gel strength, than is usually used in the maintenance phase of somatic embryogenesis, has a beneficial effect on the maturation of *P. strobus* somatic embryos with respect to the number of somatic embryos per FW embryogenic tissue, germination and plant conversion frequency. This beneficial effect is due to the concomitant decrease in water availability to the embryogenic tissues which is manifested in reduced water potential in the embryogenic tissue and developing somatic embryos.

To determine if maturation medium with increased gel strength would procure similar response in other than Pinus strobus conifer species, a series of maturation experiments was carried out with a number of conifer embryogenic tissues on ½ LM medium gelled with agar or gellan gum at various conentrations and supplemented with several levels of ABA. In some of the species a comparison was made between medium with high gel strength versus semi-solid (0.4% gellan gum) or liquid medium containing PEG MW 4000 as additional solute. Handling of the embryogenic tissues for the maturation experiments and the culture technique were the same as described in Example 1. All the cultures were maintained on ½ LM medium with 0.4% gellan gum (Phytage™, Sigma) by subculturing onto fresh medium every 14 days. For the maturation experiments cultures not older than 10 days, preferably seven days old were used. The tissue was not subcultured during the duration of maturation. Mature somatic embryos were germinated on ½ LM medium with 2% sucrose and 0.4% gellan gum (Phytagel™). Germination vigor was evaluated after 3 weeks. Water potential measurements were done on embryogenic tissue and somatic embryos of Douglas fir and interior spruce cultured on maturation media with various concentrations of gellan gum (Phytagel™).

Pseudotsuga menziesii:

Table 7 shows results on somatic embryo maturation and germination of line 5001. The number of mature somatic embryos was positively correlated to the increased concentration of agar or gellan gum in the medium. Somatic embryos matured on media with high gelling agent concentration attained high germination frequencies. No maturation of somatic embryos occurred on medium with 0.4% gellan gum.

Table 8 shows water potential values of embryogenic tissue and somatic embryos when cultured on medium with varied concentrations of gellan gum. Similarly to Pinus strobus (as described in Example 3), the water potential of embryogenic tissue after one week of culture was in an equilibrium with the water potential of the media, −0.44±0.04 MPa and −0.43±0.01 MPa respectively. After 2 weeks, clear trends in the water potential of embryogenic tissues were established. The tissue cultured on maturation medium with 1.0% gellan gum had significantly lower water potentials than those of tissues cultured on lower gellan gum concentrations. This trend was maintained through week 4 and by week 8, the water potential of mature somatic embryos from medium with 1.0% gellan gum was significantly lower than those from medium with lower gellan gum concentrations. At week 10, the trends remained the same.

Pinus banksiana:

Table 9 shows the effects of manipulating the water potential of the growth environments on somatic embryo maturation and germination of Pinus banksiana line 545. Five concentrations of gellan gum (Phytagel), and three concentrations of ABA were tested with each gellan gum concentration. A clear upward trend in the numbers of mature somatic embryos produced on media containing increased concentrations of gellan gum was observed. It was also beneficial to increase ABA level from 40 μM to 80 μM. Relatively high frequency of germination (>70%) was achieved from somatic embryos that matured on medium with 1.0 or 1.2% gellan gum.

Pinus taeda:

Table 10 shows the effects of manipulating the water potential of the growth environments on somatic embryo maturation and germination of Pinus taeda line A. Three gellan gum concentrations each with 120 μM ABA were tested in the maturation media. Medium with gellan gum at 0.8% supported maturation of relatively high number of somatic embryos that displayed germination frequency of over 50%. As gellan gum was further increased, the somatic embryos displayed lower germination frequency.

Picea glauca x engelmannii:

Tables 11 and 12 show the effects of manipulating the water potential of the growth environments on somatic embryo maturation and germination of Picea glauca x engelmannii lines 4-2809 and 10-1418. Liquid medium with PEG 4000 and 60 μM ABA was tested against semi-solid media gelled with different concentrations of gellan gum (Phytagel™) and 60 μM ABA. The numbers of mature somatic embryos were always higher on media solidified with gellan gum compared to liquid medium with PEG. In order to test PEG at 15%, it was necessary to use liquid medium because upon addition of gellan gum, the medium would not solidify. The most pronounced effect of both media (liquid with PEG versus gelled medium without PEG) was manifested in the germination response. Low numbers or no normal germinants were recovered from somatic embryos matured on PEG medium (Table 12) and those that matured on medium with 0.25% gellan gum as opposed to the media with high gellan gum level (0.75%) (Table 11).

Table 13 shows water potential of embryogenic tissue and somatic embryos when cultured on media with varied concentrations of gellan gum. Similarly to *Pinus strobus* and *Pseudotsuga manziesii*, interior spruce embryogenic tissue cultured on the maturation media solidified with various concentrations of gellan gum showed decreased water potential on media with high concentration of gellan gum (0.6 and 0.7% versus 0.4%). In this species however, the trend was established sooner than in the other two species because it was distinct after the first week of culture as opposed to 2 weeks. While the embryogenic tissue and mature somatic embryos displayed high water potential on medium with 0.4% gellan gum, the water potentials in cultures grown on medium with high gellan gum were significantly lower.

Picea sitchensis:

Table 14 shows results on somatic embryo maturation and germination of line FB2-253 on medium gelled with gellan gum with and without PEG. High numbers of mature somatic embryos were obtained on all the media however the highest germination frequency was attained from somatic embryos matured on medium without PEG. Somatic embryos matured on either 0.6 or 0.7% gellan gum germinated at 80–90%.

TABLE 7

Maturation of somatic embryos of Douglas fir (*Pseudotsuga menziesii*, line 5001) after 10 weeks on ½ LM medium containing 3% sucrose, 120 μM ABA and various concentrations of gelling agents.

| Gelling agent (%) | No. of somatic embryos $g^{-1}$ FW tissue | Germination (%) |
|---|---|---|
| Agar Difco-Noble ® | | |
| 0.8 | 0 | n/a |
| 1.6 | 25 | 95 |
| 2.0 | 200 | 97 |
| Gellan gum Phytagel ™ | | |
| 0.4 | 0 | n/a |
| 0.8 | >250 | >90 |
| 1.0 | >250 | >90 |

TABLE 8

Water potential of Douglas fir (*Pseudotsuga menziesii*, line 5001) embryogenic cultures on ½ LM maturation medium containing 3% sucrose, 120 μM ABA and various concentrations of gellan gum (Phytagel ™)

| Gellan gum (%) | Water potential (MPa) | | | | |
|---|---|---|---|---|---|
| | 1 wk | 2 wks | 4 wks | 8 wks | 10 wks |
| 0.4 | −0.46 | −0.25 ± 0.06 | −0.16 ± 0.00 | no maturation | no maturation |
| 0.6 | −0.38 | −0.29 ± 0.04 | −0.27 ± 0.04 | −0.22 ± 0.04 | precocious |
| 0.8 | −0.46 | −0.39 ± 0.06 | −0.34 ± 0.03 | −0.36 ± 0.07 | −0.38 ± 0.02 |
| 1.0 | −0.45 | −0.56 ± 0.05 | −0.52 ± 0.02 | −0.50 ± 0.04 | −0.55 ± 0.05 |
| Mean | −0.44 ± 0.04 | | | | |

Note: From 1 to 4 wks the water potential measurements were made on embryogenic tissue plus developing somatic embryos. From week 6 the water potential was determined in somatic embryos only.

TABLE 9

Maturation of somatic embryos of jack pine (*Pinus banksiana*, line 545) after 8 weeks on ½ LM medium with 3% sucrose, different concentrations of ABA and gellan gum (Phytagel ™).

| Gellan gum (%) | ABA (μM) | No. of mature somatic embryos $g^{-1}$ FW tissue | Germination (%) |
|---|---|---|---|
| 0.4 | 0 | 0 | n/a |
| 0.4 | 80 | 0 | n/a |
| 0.4 | 120 | 0 | n/a |
| 0.6 | 40 | 0 | n/a |
| 0.6 | 60 | 0 | n/a |
| 0.6 | 80 | 0 | n/a |
| 0.7 | 40 | 10 | n/a |
| 0.7 | 60 | 33 | >50 |
| 0.7 | 80 | 66 | >50 |
| 1.0 | 40 | >165 | >70 |
| 1.0 | 60 | >165 | >70 |
| 1.0 | 80 | >165 | >70 |
| 1.2 | 40 | >165 | >70 |
| 1.2 | 60 | >165 | >70 |
| 1.2 | 80 | >165 | >70 |

TABLE 10

Maturation of somatic embryos of loblolly pine (*Pinus taeda*, line A) after 10 weeks on ½ LM medium with 3% sucrose, 120 uM ABA and various concentrations of gellan gum (Phytagel ™).

| Gellan gum (%) | No. of mature somatic embryos g$^{-1}$ FW tissue | Germination (%) |
|---|---|---|
| 0.4 | 43 | 31 |
| 0.8 | 185 | 57 |
| 1.0 | 162 | 33 |

TABLE 11

Maturation of somatic embryos of interior spruce (*Picea glauca × engelmannii*, line 4-2809) after 6 weeks on ½ LM medium with 3% sucrose, 60 μM ABA and gellan gum (Phytagel ™ ).

| Gellan gum (%) | No. of mature somatic embryos g$^{-1}$ FW tissue | Germination (%) |
|---|---|---|
| 0.25 | 752 ± 330 | 27 ± 14 |
| 0.5 | 600 ± 185 | 65 ± 6 |
| 0.75 | 514 ± 99 | 70 ± 16 |

TABLE 12

Maturation of somatic embryos of interior spruce (Picea × *engelmannii*, line 10-1418) after 9 weeks on ½ LM medium with 3% sucrose, 60 μM ABA and gellan gum (Phytagel ™ ) and on liquid ½ LM medium with 60 μM ABA, 3% sucrose and PEG 4000. On the latter medium the tissue was placed on the filter paper which was placed on the nylon screen (500 μm pore size) which was placed over container with liquid medium in such a way that the nylon screen was touching the surface of the medium.

| Gellan gum (%), PEG (%) | No. of mature somatic embryos g$^{-1}$ FW tissue | Germination (%) |
|---|---|---|
| Gellan gum | | |
| 0.4 | 500 ± 130 | n/t |
| 0.6 | 805 ± 55 | n/t |
| 0.7 | 950 ± 125 | 91 ± 8 |
| Liquid | | |
| 7.5 PEG | 40 | 7 |
| 15 PEG | 145 | 0 |

TABLE 13

Water potential of interior spruce (*Picea glauca × engelmannii*, line 10-1418) on ½ LM maturation medium with 3% sucrose, 60 μM ABA and various concentrations of gellan gum (Phytagel ™ ).

| Water potential (MPa) Gellan gum (%) | 1 wk | 2 wks | 4 wks | 6 wks | 8 wks |
|---|---|---|---|---|---|
| 0.4 | −0.47 ± 0.05 | −0.33 ± 0.06 | −0.31 × 0.01 | −0.27 ± 0.02 | −0.20 ± 0.04 |
| 0.6 | −0.52 ± 0.02 | −0.47 ± 0.03 | −0.47 ± 0.02 | se not mature | −0.54 ± 0.06 |
| 0.7 | −0.50 ± 0.02 | −0.51 ± 0.02 | −0.50 ± 0.02 | se not mature | −0.57 ± 0.07 |

Note:
From 1 to 4 wks the water potential measurements were made on embryogenic tissue plus developing somatic embryos. From week 6 the water potential was determined in somatic embryos only.

TABLE 14

Maturation of somatic embryos of sitka spruce (*Picea sitchensis*, line FB2-253) after 9 weeks on ½ LM medium with 3% sucrose, 60 μm ABA and gellan gum (Phytagel ™ ).

| Gellan gum, (%), PEG (%) | No of mature somatic embryos g$^{-1}$ FW tissue | Germination (%) |
|---|---|---|
| 0.6 gellan gum | 310 ± 95 | 83 ± 7 |
| 0.7 gellan gum | 240 ± 110 | 92 ± 10 |
| 0.4 gellan gum, 5 PEG | 315 ± 270 | 33 ± 6 |
| 0.4 gellan gum, 8 PEG | 430 ± 60 | 40 ± 5 |

EXAMPLE 5

A test was carried out using apparatus as shown in FIG. 2 of the drawings to determine the effect of height from the liquid level in the type of apparatus that uses a porous support to manipulate the water potential.

The apparatus consisted of an enclosed container 25 holding a body 26 of liquid medium having a depth of about 2 cm. Positioned within the container was a block of dense porous foam material 27 having a sloping upper surface 28 positioned above the upper level of the body of growth medium. Embryogenic tissue was placed on the sloping upper surface at three positions 29, 30 and 31 (referred to below as Position 1, Position 2 and Position 3, respectively). The positions were chosen so that the samples were located, respectively, 2.6 cm, 3.5 cm and 4.0 cm above the upper level of the liquid medium. After a period of culturing, the number of embryos produced from each sample of embryogenic tissue were counted. The results are as shown in Table 15.

The results show that the number of embryos increased as the height above the liquid increased for the first two positions, but decreased for the third position. This may be because there is a critical height at which the capillary action of the foam pores can no longer draw up sufficient nutrient for embryo maturation. This indicates that there is an optimum spacing above the liquid that reduces the water potential sufficiently, while still allowing sufficient nutrient absorption for proper embryo maturation. The optimum height may be determined from experiments such as the above. Clearly, embryo maturation apparatus would be designed to provide the support surface at the optimum height, which is likely to depend on the porosity and cavitational properties of the physical support material and perhaps the plant species of the embryos concerned and the solute composition of the liquid medium.

TABLE 15

Somatic embryos produced on the sloping surface of a porous solid subtrate; cultures were positioned at three different heights above the liquid growth medium.

| Slant Format (dense foam) | Position 1 | Position 2 | Position 3 |
| --- | --- | --- | --- |
| Height Above Media (cm) | 2.6 | 3.5 | 4.0 |
| Embryos Produced (#) | 25 | 90 | 4 |

NB: Position 1 is closest to the medium while Position 3 is farthest from the medium

EXAMPLE 6

A test similar to that reported in Example 5 was carried out, except for using three blocks of coarse foam material (referred to below as Block 1, Block 2 and Block 3), each having horizontal upper surfaces and different thicknesses, resulting in different heights of the upper surfaces from the liquid level, as shown in FIG. 3. Samples of embryogenic tissue were placed on each foam block and the number of developed embryos were counted after a suitable period of maturation. The results are shown on Table 16.

Again, a similar effect of inreased embryo production with height up to an optimum height was observed. However, in this case, the optional height is lower than the optional height on the dense foam support used in Example 5, due to the increased porosity and subsequent decreased capillarity in the coarse foam.

TABLE 16

Somatic embryos produced on the horizontal surfaces of porous solid subtrates.

| Horizontal Format (coarse foam) | Block 1 | Block 2 | Block 3 |
| --- | --- | --- | --- |
| Height Above Media (cm) | 1 | 2 | 3 |
| Embryos Produced (#) | 59 | 78 | 6 |

We claim:

1. A method of developing and maturing plant somatic embryos in a growth environment having a water potential relative to the embryos, which method comprises exposing an embryogenic culture of embryogenic tissue or developing and maturing embryos to a maturation medium, and allowing said embryogenic culture to develop into mature somatic embryos characterized in that a physical means is associated with the medium to reduce the availability of water in the growth environment for uptake by said embryogenic culture, wherein the physical means is selected from the group comprising (I) a gelling agent in a strength of at least about 800 g cm$^{-2}$, and (ii) a porous support separating said culture from direct contact with said medium and providing to embryos in contact therewith a water stress.

2. A method according to claim 1, characterized in that the embryogenic culture is from a genus of angiosperm species.

3. A method according to claim 1, characterized in that the embryogenic culture is from a genus of gymnosperm species.

4. A method according to claim 1, characterized in that the embryogenic culture is selected from the genus Pinus, and the availability of water is reduced such that the resulting water potentials of the embryogenic tissue or developing and maturing embryos are less than –0.20 MPa.

5. A method according to claim 4, characterized in that said resulting water potentials are in the range of –0.43 MPa to –0.70 MPa.

6. A method according to claim 1, characterized in that the embryogenic culture is selected from the genus Picea, and the availability of water in the growth environment is reduced such that the resulting water potentials of the embryogenic tissue or developing and maturing embryos are less than –0.20 MPa.

7. A method according to claim 6, characterized in that the resulting water potentials are in the range of –0.43 MPa to –0.70 MPa.

8. A method according to claim 1, characterized in that the embryogenic culture is selected from the genus Pseudotsuga and the availability of water in the growth environment is reduced such that the resulting water potentials of the embryogenic tissue or developing and maturing embryos are less than –0.20 MPa.

9. A method according to claim 8, characterized in that the resulting water potentials are in the range of –0.43 MPa to –0.70 MPa.

10. The method of claim 1, wherein the physical means of affecting the availability of water in the growth environment comprises placing the embryogenic culture on a porous support within a culture vessel, said support being positioned in a liquid medium within the vessel such that the culture is not in direct contact with the liquid medium.

11. A method according to claim 1, further comprising increasing the concentration of gelling agent in the maturation medium without affecting the concentrations of solutes within the medium.

12. A method according to claim 1 wherein the physical means is a porous support within a culture vessel and further comprising manipulating the availability of water for uptake during the development and maturation of somatic embryos in a culture vessel, which comprises placing a liquid maturation medium in the vessel, positioning a porous support carrying a culture of the embryos on the liquid medium such that there is no direct contact between the medium and the culture, sealing the vessel with a cover, and allowing said embryos to develop and mature.

13. A method of claim 1 characterized in that the porous support is selected from the group consisting of natural and synthetic foams, sponges, fibres, membranes and filters.

14. A method of claim 1 characterized in that said porous support is made of a material having a gradient of matric water potential that results in a suitably reduced water potential for proper development and maturation of the embryos.

15. A method of claim 1 characterized in that the availability of water for uptake within the culture vessel is manipulated by the separation of the embryo culture from a liquid medium, the availability of said water being controllable by the porosity of a material of which the porous support is formed, and the height of the culture above the liquid medium.

16. The method of claim 12, wherein the somatic embryos are from genera of angiosperm species.

17. The method of claim 12, wherein the somatic embryos are from genera of gymnosperm species.

18. A method according to claim 1, additionally comprising the steps of removing the embryos from the maturation medium and drying the embryos in an atmosphere having a relative humidity less than 99.9%.

19. A method according to claim 1, additionally comprising the steps of removing the embryos from the maturation medium and drying the embryos in an atmosphere having a relative humidity from 85% to 99%.

20. A method according to claim 1, characterized in that the somatic embryos are selected from the species *Pinus radiata*.

21. A method according to claim 1, characterized in that the gelling agent is selected from the group consisting of gellan gum, agar, agarose, and cross-linked alginates.

22. A method according to claim 11, characterized in that the gelling agent is gellan gum of a concentration between about 0.9% to about 1.2%.

23. A method according to claim 1, wherein the physical means is a porous support within a culture vessel, said support being positioned in a liquid medium within the vessel such that the culture is not in direct contact with the liquid medium.

24. A method of developing and maturing somatic embryos, the method comprising maturing an embryogenic culture of embryogenic tissue or developing and maturing embryos in the presence of a suitable maturation medium, characterized in that the medium comprises a gelling agent in a strength of at least about 800 g cm$^{-2}$ for reducing the water available for uptake by the embryos.

* * * * *